(12) United States Patent
Udagawa et al.

(10) Patent No.: US 10,117,853 B2
(45) Date of Patent: **\*Nov. 6, 2018**

(54) CYCLIC AMINE DERIVATIVE AND PHARMACEUTICAL USE THEREOF

(71) Applicant: Toray Industries, Inc., Tokyo (JP)

(72) Inventors: Shuji Udagawa, Kamakura (JP);
Yasuhiro Morita, Kamakura (JP);
Naoki Izumimoto, Kamakura (JP);
Katsuhiko Iseki, Kamakura (JP);
Shunsuke Iwano, Kamakura (JP);
Tomoya Miyoshi, Kamakura (JP); Yuji Osada, Iyo-gun (JP); Tetsuro Koreeda, Kamakura (JP); Masanori Murakami, Kamakura (JP); Motohiro Shiraki, Kamakura (JP); Kei Takahashi, Kamakura (JP); Keiyu Oshida, Kamakura (JP); Eriko Higashi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,581

(22) PCT Filed: Mar. 24, 2016

(86) PCT No.: PCT/JP2016/059298
§ 371 (c)(1),
(2) Date: Sep. 22, 2017

(87) PCT Pub. No.: WO2016/152955
PCT Pub. Date: Sep. 29, 2016

(65) Prior Publication Data
US 2018/0104221 A1    Apr. 19, 2018

(30) Foreign Application Priority Data
Mar. 24, 2015    (JP) .................. 2015-061248

(51) Int. Cl.
| | |
|---|---|
| *C07D 413/14* | (2006.01) |
| *C07D 403/06* | (2006.01) |
| *A61K 31/4178* | (2006.01) |
| *A61K 31/4025* | (2006.01) |
| *A61K 31/5377* | (2006.01) |
| *C07D 401/06* | (2006.01) |
| *A61P 25/04* | (2006.01) |
| *A61P 29/02* | (2006.01) |

(52) U.S. Cl.
CPC ...... *A61K 31/4178* (2013.01); *A61K 31/4025* (2013.01); *A61K 31/5377* (2013.01); *A61P 25/04* (2018.01); *A61P 29/02* (2018.01); *C07D 401/06* (2013.01); *C07D 403/06* (2013.01); *C07D 413/14* (2013.01)

(58) Field of Classification Search
CPC ............ A61K 31/4178; A61K 31/4025; A61K 31/5375; C07D 403/06; C07D 413/14
See application file for complete search history.

(56) References Cited

U.S. PATENT DOCUMENTS

2016/0194302 A1 *  7/2016  Morita ................. A61K 31/454
514/235.8

FOREIGN PATENT DOCUMENTS

| | | |
|---|---|---|
| FR | 2 567 885 A1 | 1/1986 |
| GB | 2 163 150 A | 2/1986 |
| JP | 2005-507906 A | 3/2005 |
| JP | 2005-527519 A | 9/2005 |
| JP | 2006-8664 A | 1/2006 |
| WO | 03/031432 A1 | 4/2003 |
| WO | 2006/137465 A1 | 12/2006 |
| WO | 2013/147160 A1 | 10/2013 |
| WO | 2-15/046403 A1 | 4/2015 |
| WO | WO2015046403 * | 4/2015 |

OTHER PUBLICATIONS

Akiko Okifuji et al. "Management of Fibromyalgia Syndrome: Review of Evidence," Pain and Therapy, vol. 2, 2013, pp. 87-104.

\* cited by examiner

*Primary Examiner* — Rebecca L Anderson
*Assistant Examiner* — Karen Cheng
(74) *Attorney, Agent, or Firm* — DLA Piper LLP, US

(57) ABSTRACT

A compound exerts a strong analgesic effect against pain, in particular, neuropathic pain and/or fibromyalgia syndrome. A cyclic amine derivative represented by general formula or a pharmacologically acceptable salt thereof:

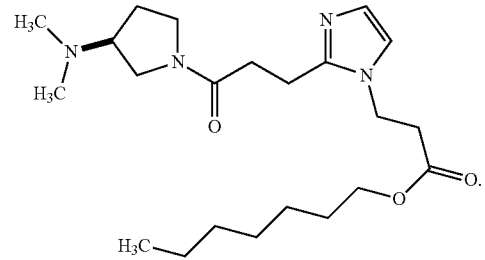

A method of treating neuropathic pain includes administering a therapeutically effective amount of the cyclic amine derivative to a mammal. A method of treating fibromyalgia syndrome includes administering a therapeutically effective amount of the cyclic amine derivative to a mammal.

12 Claims, 11 Drawing Sheets

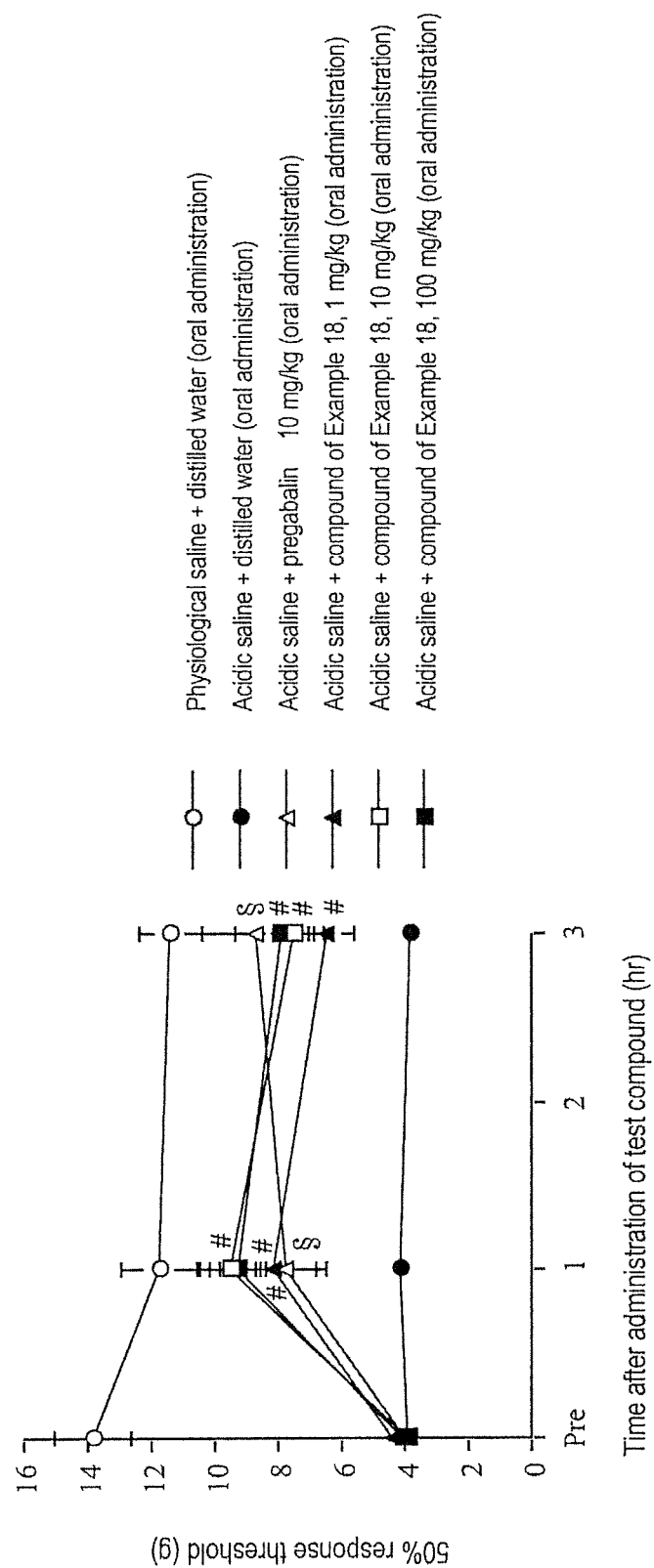

CYCLIC AMINE DERIVATIVE AND PHARMACEUTICAL USE THEREOF

TECHNICAL FIELD

This disclosure relates to a cyclic amine derivative and pharmaceutical use thereof.

BACKGROUND

Pain is an unpleasant sensory and emotional experience associated with actual or potential tissue damage. Pain is classified according to cause into nociceptive pain, neuropathic pain and psychogenic pain. As pain caused by an unknown cause, fibromyalgia syndrome is known.

Neuropathic pain is pathological pain caused by peripheral or central nervous system dysfunction, more specifically, pain caused by e.g., direct damage and oppression of the nerve tissue despite of no nociceptive stimulus to a nociceptor. As a therapeutic agent for neuropathic pain, an anticonvulsant, an antidepressant, an anxiolytic drug or an antiepileptic drug (gabapentin, pregabalin or the like) is used.

Fibromyalgia syndrome is a disorder in which systemic pain is the leading symptom and neuropsychiatric and neurovegetative symptoms are the secondary symptoms. As therapeutic agents for fibromyalgia syndrome, pregabalin, which has been approved in the United States and Japan, duloxetine and milnacipran, which have been approved in the United States, are principally used. Also, drugs not approved as a therapeutic agent for fibromyalgia syndrome, i.e., a nonsteroidal anti-inflammatory agent, an opioid compound, an antidepressant, an anticonvulsant and an antiepileptic drug are used. However, nonsteroidal anti-inflammatory agents and opioid compounds are generally said to have a low therapeutic effect (Pain and Therapy, Vol. 2, p. 87-104, 2013).

Other than these, French Patent 2 567 885 discloses that substituted piperidines have a cardiotonic activity. JP Patent Publication (Kokai) No. 2006-008664 discloses that imidazole derivatives have an FXa inhibitory effect. International Publication WO 2003/031432 discloses that substituted piperidines have a potential drug efficacy against overweight or obesity. International Publication WO 2013/147160 discloses that an imidazole derivative has an analgesic action.

However, as therapy with a conventional therapeutic agent for neuropathic pain is highly frequently associated with central nervous system adverse effects (e.g., dizziness, nausea or vomiting), long-term administration is difficult. Thus, development of a novel therapeutic agent for neuropathic pain has been desired.

Pregabalin, duloxetine and milnacipran, which have been approved as therapeutic agents for fibromyalgia syndrome, fail to provide a clinically satisfactory therapeutic effect against fibromyalgia syndrome and their drug efficacy significantly varies among patients. In the context, it has been strongly desired to develop a novel therapeutic agent for fibromyalgia syndrome having a sufficient therapeutic effect.

Further, FR '885 suggests that the substituted piperidines described therein have an efficacy for migraine and WO '160 discloses that the imidazole derivative described therein has an analgesic action. However, neither disclosure of the cyclic amine derivative having an analgesic action nor suggestion on the relevancy of an analgesic action to a chemical structure is provided. JP '664 describes imidazole derivatives and WO '432 describes substituted piperidines. Neither disclose nor suggest analgesic action of their respective compounds.

Thus, it could be helpful to provide a compound having a strong analgesic action for pain, in particular, neuropathic pain and/or fibromyalgia syndrome.

SUMMARY

We found a cyclic amine derivative having a strong analgesic effect against pain, in particular, neuropathic pain and/or fibromyalgia syndrome.

More specifically, we provide a cyclic amine derivative represented by general formula (I) or a pharmacologically acceptable salt thereof:

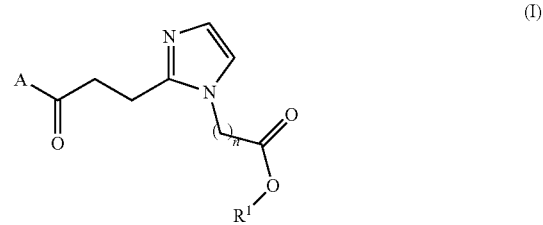

(I)

wherein A represents a group represented by formula (IIa) or (IIb),

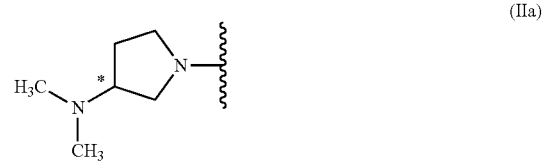

(IIa)

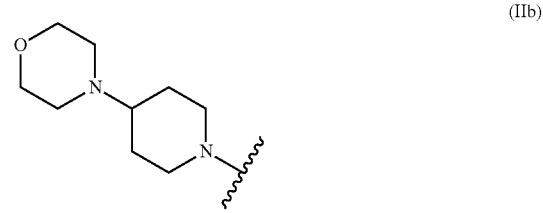

(IIb)

wherein the stereochemical configuration of the asymmetric carbon marked with * is S, $R^1$ represents an alkyl group having 3 to 8 carbon atoms; when A represents a group represented by formula (IIa), n represents 2; and when A represents a group represented by formula (IIb), n represents 1.

In the cyclic amine derivative, A preferably represents a group represented by formula (IIa). The cyclic amine derivative is more preferably a compound selected from the group consisting of n-butyl (S)-3-(2-(3-(3-(dimethylamino)pyrrolidin-1-yl)-3-oxopropyl)-1H-imidazol-1-yl)propanoate, n-hexyl (S)-3-(2-(3-(3-(dimethylamino)pyrrolidin-1-yl)-3-oxopropyl)-1H-imidazol-1-yl)propanoate, n-heptyl (S)-3-(2-(3-(3-(dimethylamino)pyrrolidin-1-yl)-3-oxopropyl)-1H-imidazol-1-yl)propanoate, and n-octyl (S)-3-(2-(3-(3-(dimethylamino)pyrrolidin-1-yl)-3-oxopropyl)-1H-imidazol-1-yl)propanoate. Analgesic action can be enhanced by defining the cyclic amine derivative as mentioned above.

Also, in the cyclic amine derivative, A is preferably a group represented by formula (IIb). The cyclic amine derivative is more preferably a compound selected from the group consisting of n-propyl 2-(2-(3-(4-morpholinopiperidin-1-yl)-3-oxopropyl)-1H-imidazol-1-yl)acetate, n-butyl 2-(2-(3-(4-morpholinopiperidin-1-yl)-3-oxopropyl)-1H-imidazol-1-yl)acetate, n-pentyl 2-(2-(3-(4-morpholinopiperidin-1-yl)-3-oxopropyl)-1H-imidazol-1-yl)acetate, n-hexyl 2-(2-(3-(4-morpholinopiperidin-1-yl)-3-oxopropyl)-1H-imidazol-1-yl) acetate, n-heptyl 2-(2-(3-(4-morpholinopiperidin-1-yl)-3-oxopropyl)-1H-imidazol-1-yl)acetate, and n-octyl 2-(2-(3-(4-morpholinopiperidin-1-yl)-3-oxopropyl)-1H-imidazol-1-yl)acetate. Analgesic action can be enhanced by defining as mentioned above.

We also provide a medicine containing a cyclic amine derivative represented by general formula (I), or a pharmacologically acceptable salt thereof as an active ingredient.

The medicine is preferably an analgesic agent, and particularly preferably a therapeutic agent for neuropathic pain or a therapeutic agent for fibromyalgia syndrome.

We also provide a pharmaceutical composition containing a cyclic amine derivative represented by general formula (I) or a pharmacologically acceptable salt thereof and e.g., a pharmacologically acceptable excipient.

We also provide a cyclic amine derivative represented by general formula (I) or a pharmacologically acceptable salt thereof for use as a medicine.

We also provide a cyclic amine derivative represented by general formula (I) or a pharmacologically acceptable salt thereof for use in pain treatment. The pain is preferably neuropathic pain or fibromyalgia syndrome.

We also provide use of a cyclic amine derivative represented by general formula (I) or a pharmacologically acceptable salt thereof for treating pain. The pain is preferably neuropathic pain or fibromyalgia syndrome.

We also provide use of a cyclic amine derivative represented by general formula (I) or a pharmacologically acceptable salt thereof in producing a medicine for treating pain. The pain is preferably neuropathic pain or fibromyalgia syndrome.

We also provide a method of treating pain including administering a therapeutically effective amount of a cyclic amine derivative represented by general formula (I) or a pharmacologically acceptable salt thereof to a patient in need thereof. The pain is preferably neuropathic pain or fibromyalgia syndrome.

As the cyclic amine derivative or a pharmacologically acceptable salt thereof has a strong analgesic effect against pain, in particular, neuropathic pain and fibromyalgia syndrome, it can be used as an analgesic agent, in particular, a therapeutic agent for neuropathic pain and/or a therapeutic agent for fibromyalgia syndrome

BRIEF DESCRIPTION OF THE DRAWINGS

FIG. 11 is a graph showing the effect of the compound of Example 18 in a rat fibromyalgia model (oral administration).

DETAILED DESCRIPTION

Figure 1:
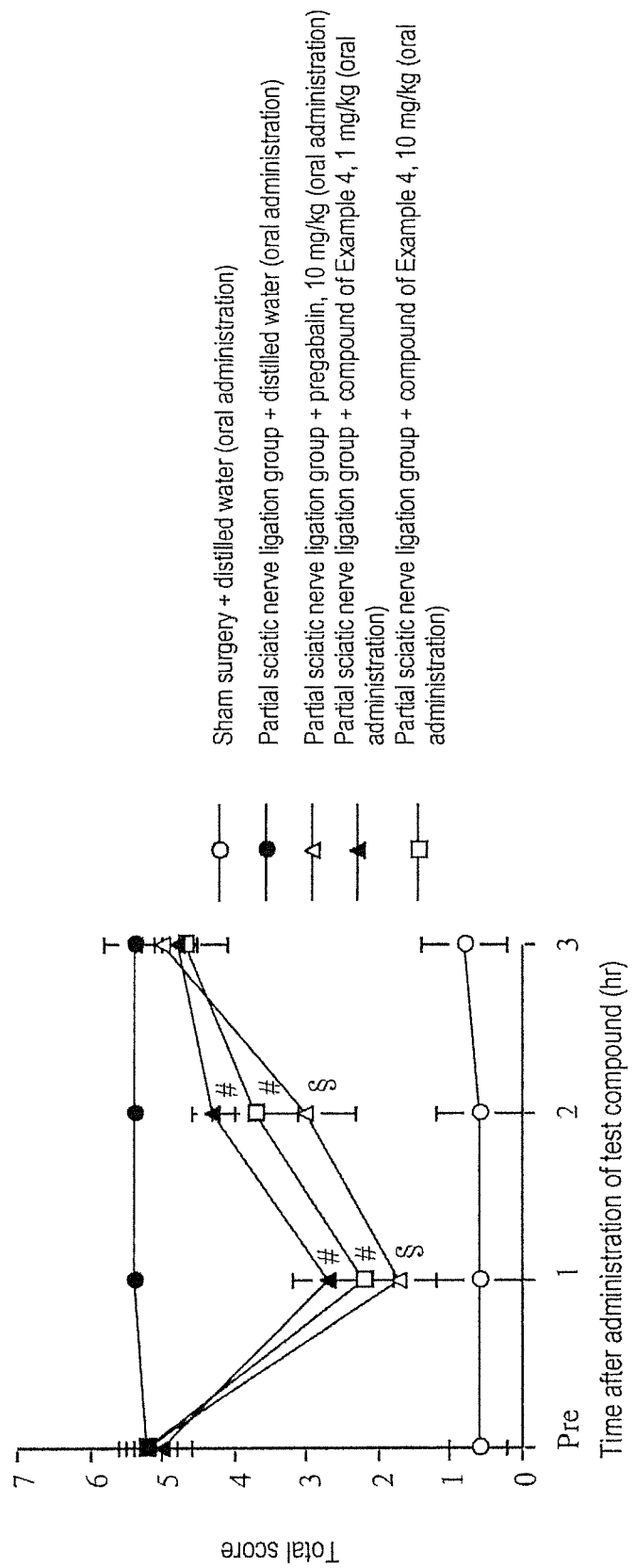
FIG. 1 is a graph showing the effect of the compound of Example 4 in a mouse partial sciatic nerve ligation model (oral administration).
Figure 2:
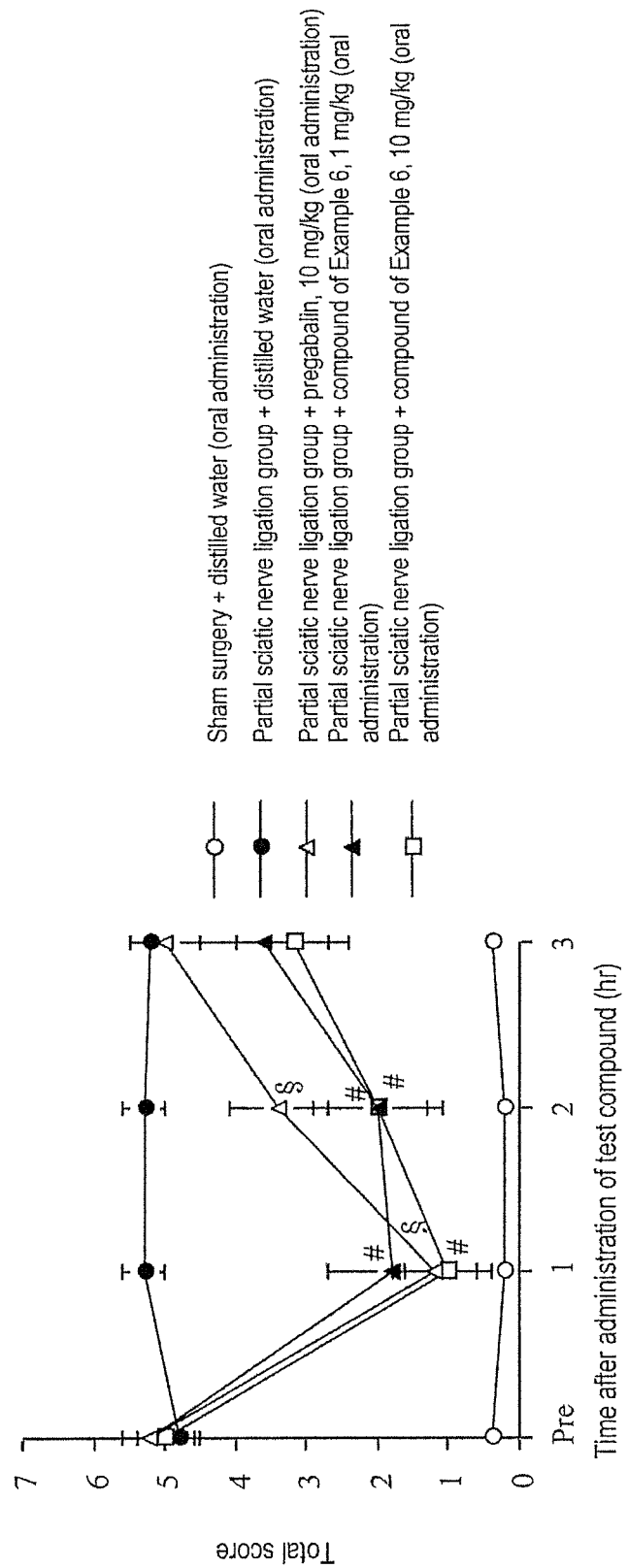
FIG. 2 is a graph showing the effect of the compound of Example 6 in a mouse partial sciatic nerve ligation model (oral administration).
Figure 3:
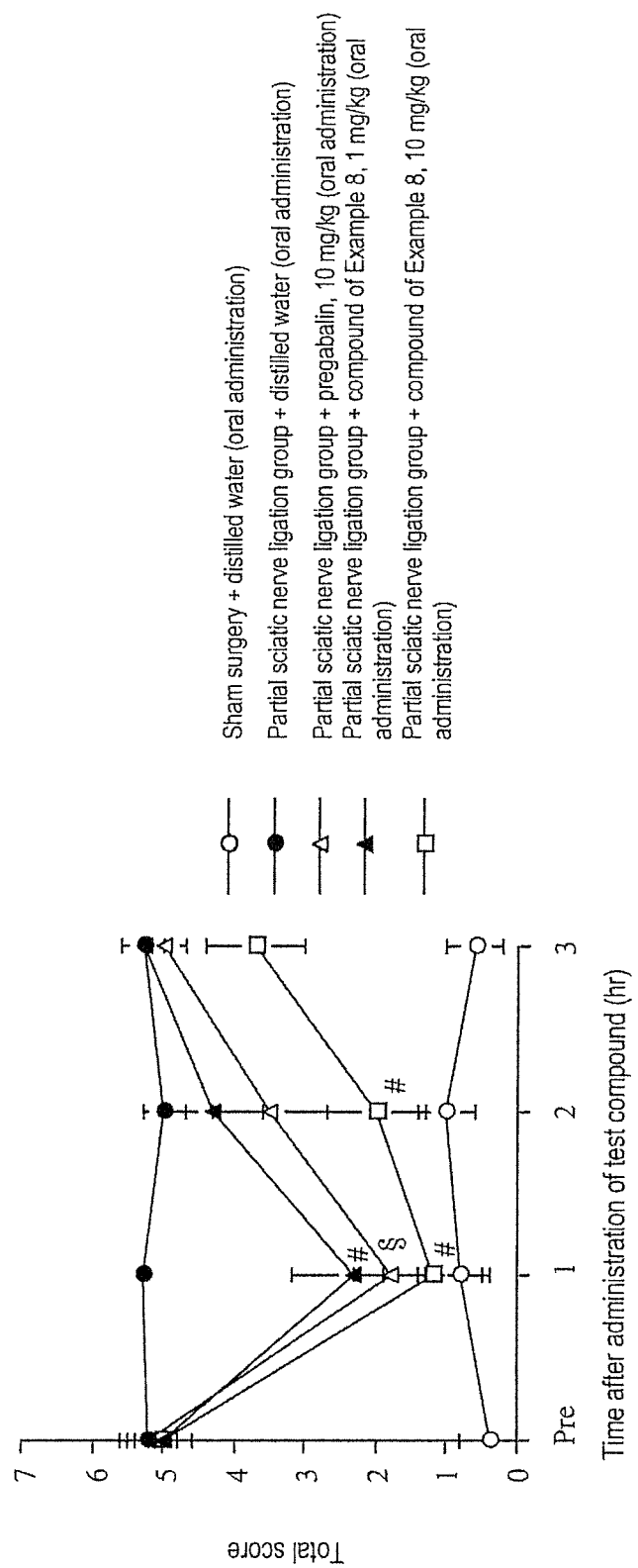
FIG. 3 is a graph showing the effect of the compound of Example 8 in a mouse partial sciatic nerve ligation model (oral administration).
Figure 4:
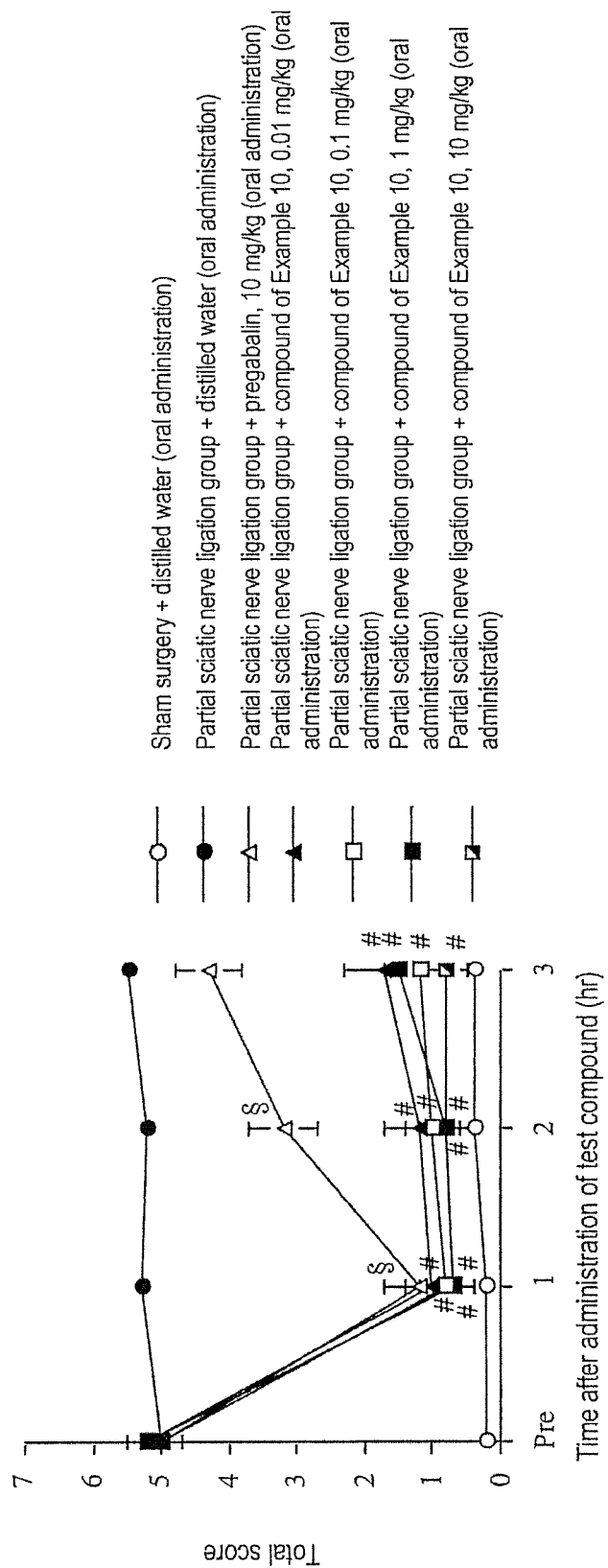
FIG. 4 is a graph showing the effect of the compound of Example 10 in a mouse partial sciatic nerve ligation model (oral administration).
Figure 5:
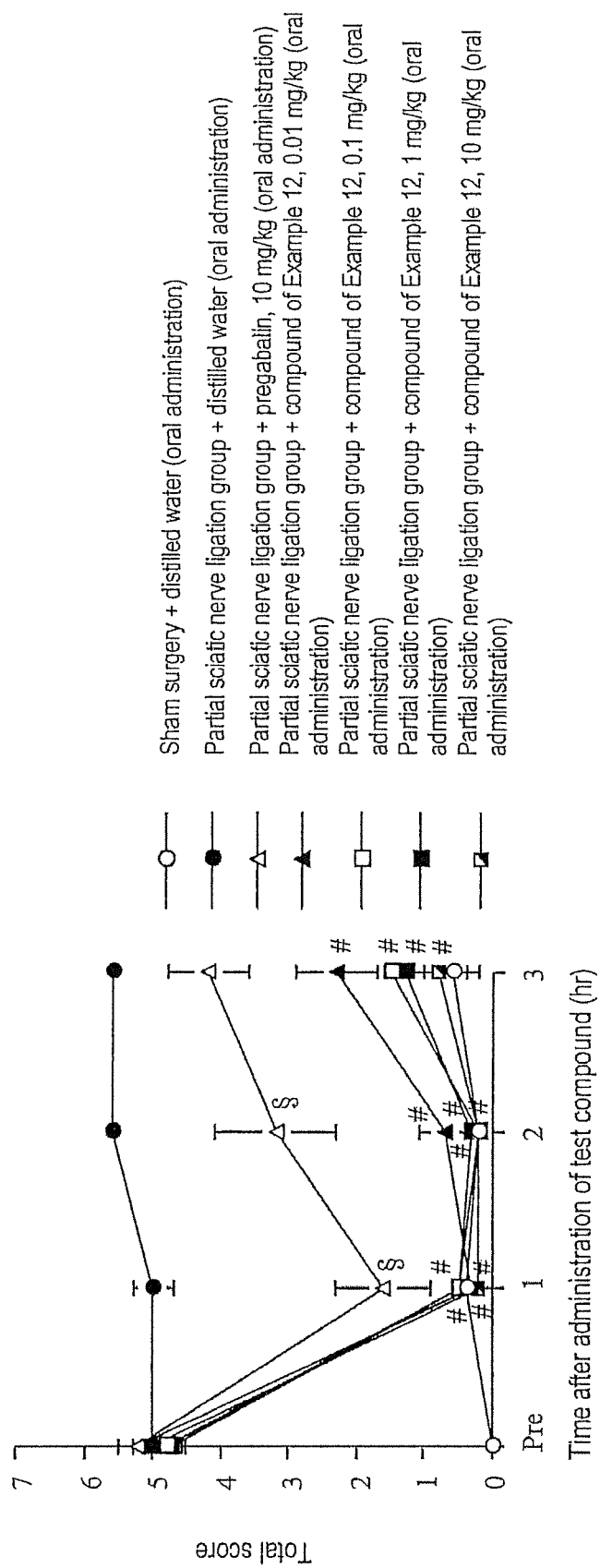
FIG. 5 is a graph showing the effect of the compound of Example 12 in a mouse partial sciatic nerve ligation model (oral administration).
Figure 6:
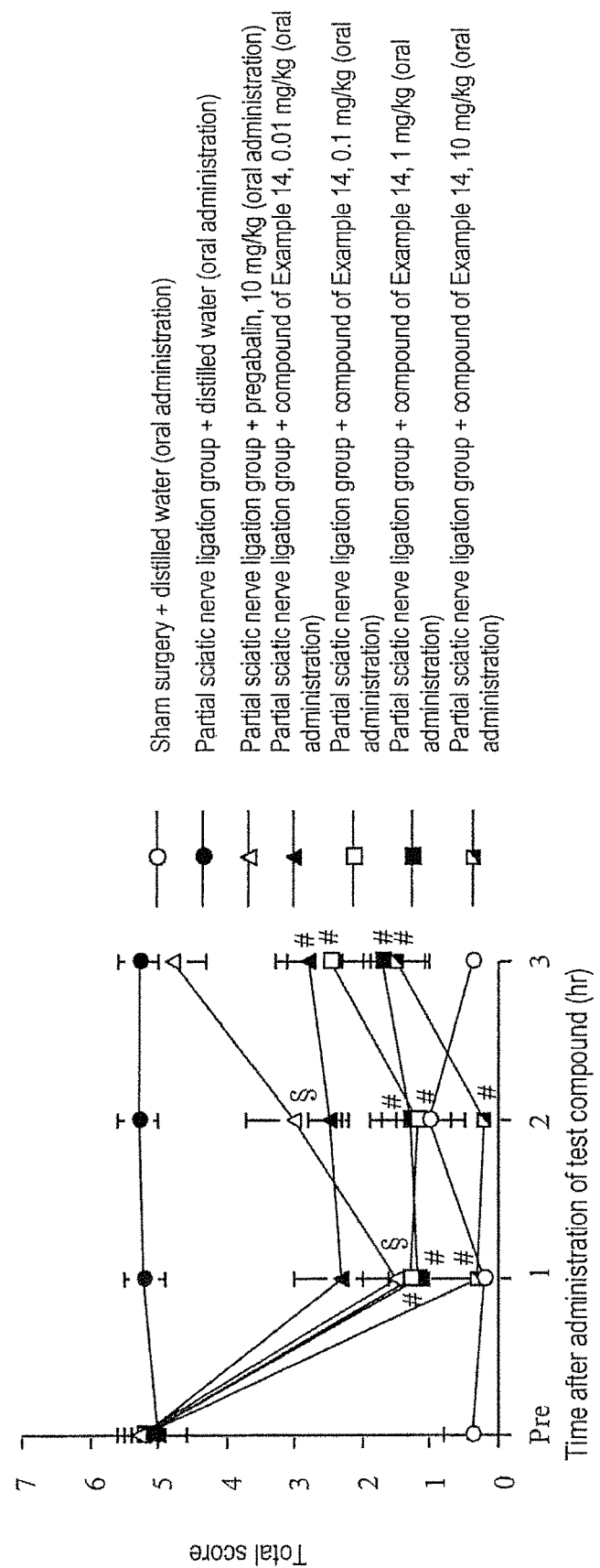
FIG. 6 is a graph showing the effect of the compound of Example 14 in a mouse partial sciatic nerve ligation model (oral administration).
Figure 7:
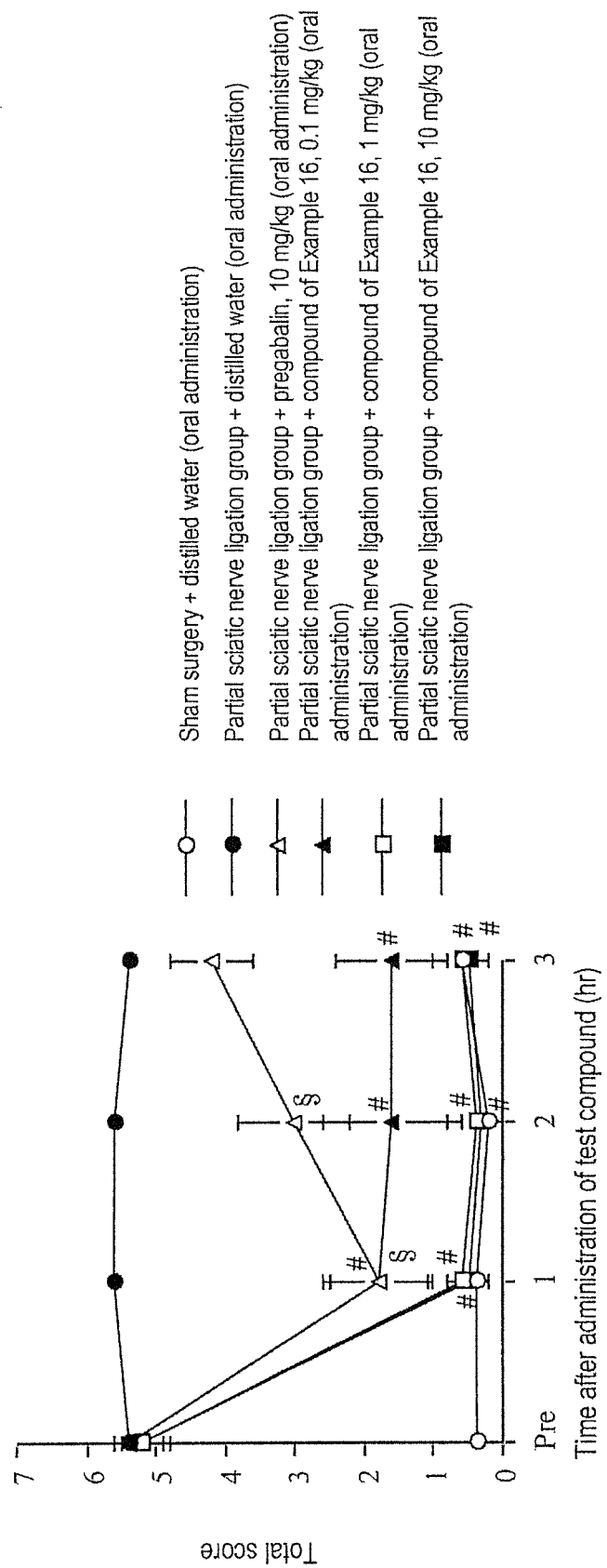
FIG. 7 is a graph showing the effect of the compound of Example 16 in a mouse partial sciatic nerve ligation model (oral administration).
Figure 8:
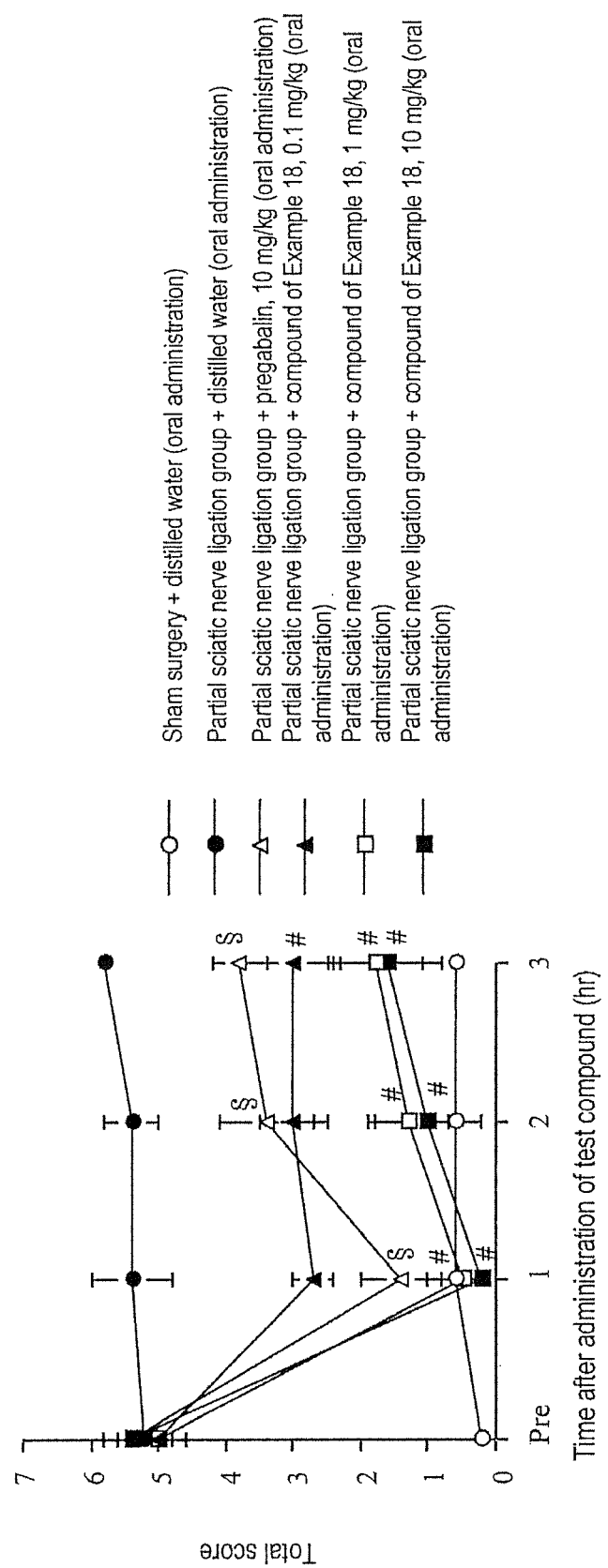
FIG. 8 is a graph showing the effect of the compound of Example 18 in a mouse partial sciatic nerve ligation model (oral administration).
Figure 9:
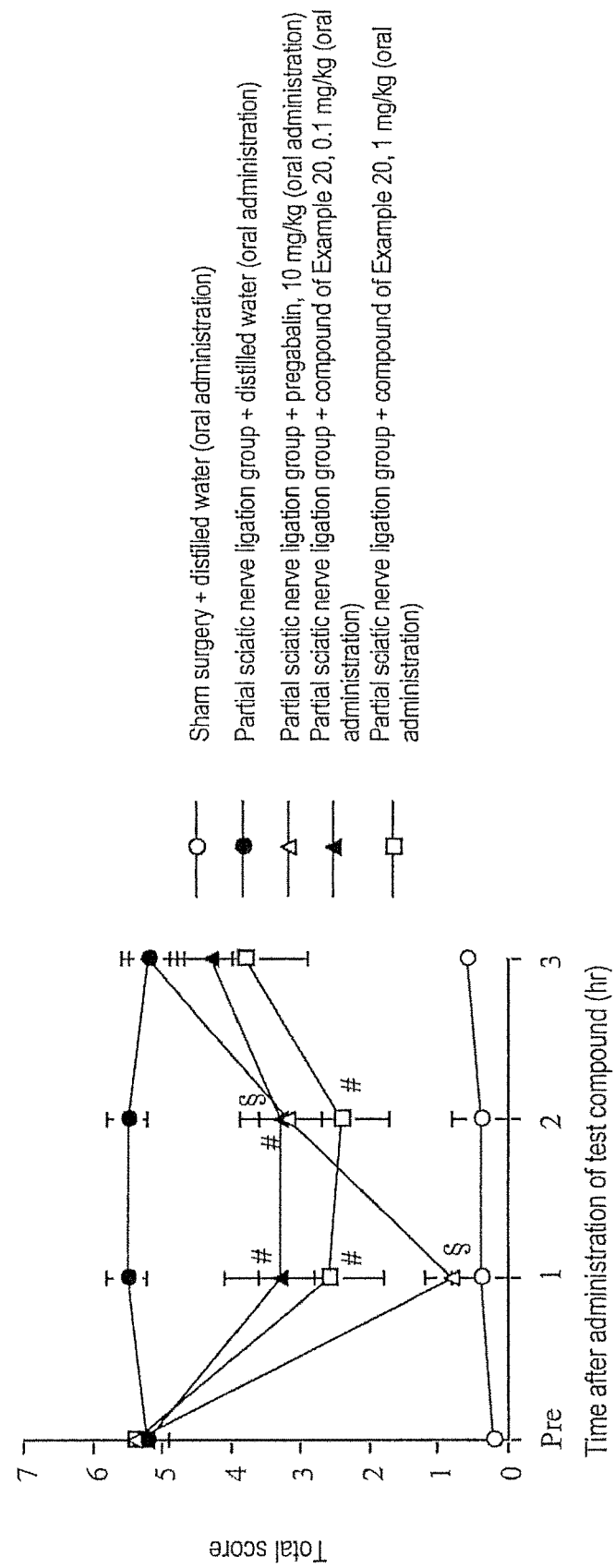
FIG. 9 is a graph showing the effect of the compound of Example 20 in a mouse partial sciatic nerve ligation model (oral administration).

The following terms used in the specification are, unless otherwise specified, defined as follows.

It is characterized in that the cyclic amine derivative is represented by general formula (I):

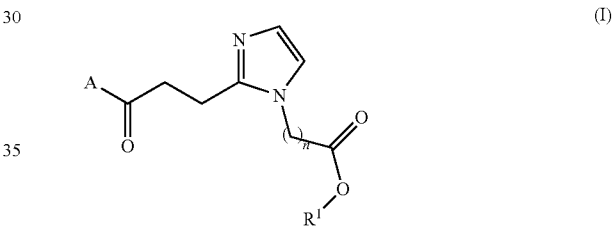

(I)

wherein A represents a group represented by formula (IIa) or (IIb),

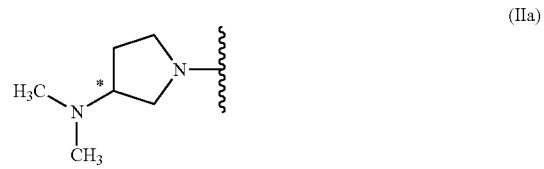

(IIa)

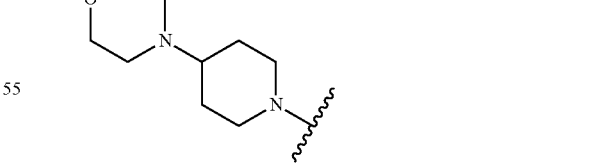

(IIb)

wherein the stereochemical configuration of the asymmetric carbon marked with * is S; $R^1$ represents an alkyl group having 3 to 8 carbon atoms; when A represents a group represented by formula (IIa), n represents 2; and when A represents a group represented by formula (IIb), n represents 1.

In the cyclic amine derivative, A preferably represents a group represented by formula (IIa). The cyclic amine derivative is more preferably a compound selected from the group consisting of n-butyl (S)-3-(2-(3-(3-(dimethylamino)pyrrolidin-1-yl)-3-oxopropyl)-1H-imidazol-1-yl)propanoate, n-hexyl (S)-3-(2-(3-(3-(dimethylamino)pyrrolidin-1-yl)-3-oxopropyl)-1H-imidazol-1-yl)propanoate, n-heptyl (S)-3-(2-(3-(3-(dimethylamino)pyrrolidin-1-yl)-3-oxopropyl)-1H-imidazol-1-yl)propanoate, and n-octyl (S)-3-(2-(3-(3-(dimethylamino)pyrrolidin-1-yl)-3-oxopropyl)-1H-imidazol-1-yl)propanoate.

Also in the cyclic amine derivative, A is preferably a group represented by formula (IIb). The cyclic amine derivative is more preferably a compound selected from the group consisting of n-propyl 2-(2-(3-(4-morpholinopiperidin-1-yl)-3-oxopropyl)-1H-imidazol-1-yl)acetate, n-butyl 2-(2-(3-(4-morpholinopiperidin-1-yl)-3-oxopropyl)-1H-imidazol-1-yl)acetate, n-pentyl 2-(2-(3-(4-morpholinopiperidin-1-yl)-3-oxopropyl)-1H-imidazol-1-yl)acetate, n-hexyl 2-(2-(3-(4-morpholinopiperidin-1-yl)-3-oxopropyl)-1H-imidazol-1-yl)acetate, n-heptyl 2-(2-(3-(4-morpholinopiperidin-1-yl)-3-oxopropyl)-1H-imidazol-1-yl)acetate, and n-octyl 2-(2-(3-(4-morpholinopiperidin-1-yl)-3-oxopropyl)-1H-imidazol-1-yl)acetate.

The "alkyl group having 3 to 8 carbon atoms" refers to a linear, branched or cyclic saturated hydrocarbon group having 3 to 8 carbon atoms; for example, a n-propyl group, an isopropyl group, a cyclopropyl group, a n-butyl group, a sec-butyl group, an isobutyl group, a tert-butyl group, a cyclobutyl group, a cyclopropylmethyl group, a n-pentyl group, a cyclopentyl group, a n-hexyl group, a cyclohexyl group, a n-heptyl group, a cycloheptyl group, a n-octyl group or a cyclooctyl group can be mentioned.

Specific examples of a preferable compound as a cyclic amine derivative represented by general formula (I) (hereinafter referred to as a cyclic amine derivative (I)) will be shown in Tables 1-1 and 1-2. However, this disclosure is not limited to these.

TABLE 1-1

| Structural formula |
| --- |
| 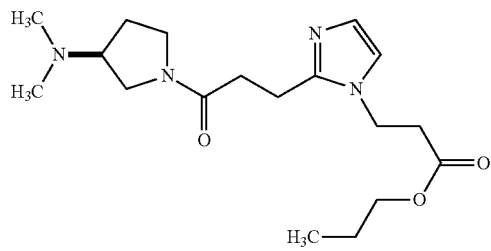 [SMILES: CCCOC(=O)CCn1ccnc1CCC(=O)N1CC[C@H](N(C)C)C1] |
| 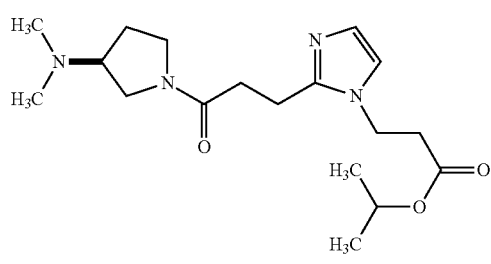 [SMILES: CC(C)OC(=O)CCn1ccnc1CCC(=O)N1CC[C@H](N(C)C)C1] |

TABLE 1-1-continued

| Structural formula |
| --- |
| 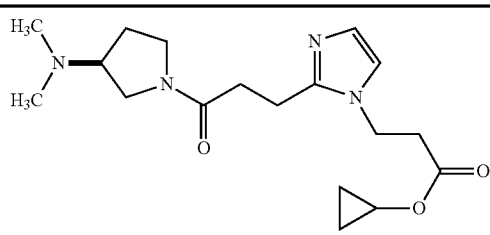 |
| 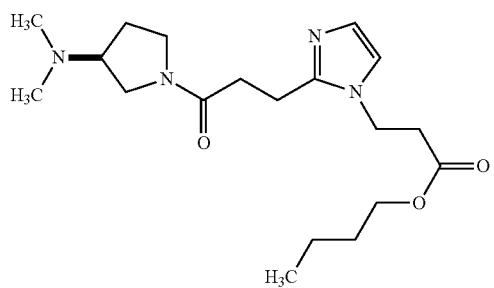 [SMILES: CCCCOC(=O)CCn1ccnc1CCC(=O)N1CC[C@H](N(C)C)C1] |
| 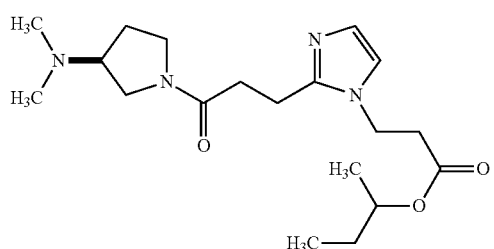 |
| 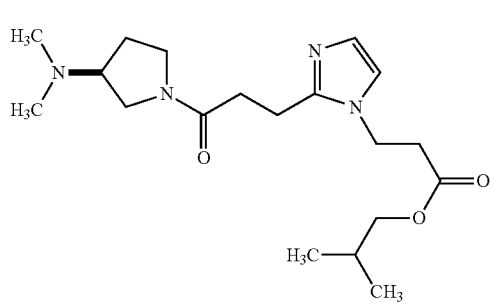 [SMILES: CC(C)COC(=O)CCn1ccnc1CCC(=O)N1CC[C@H](N(C)C)C1] |
| 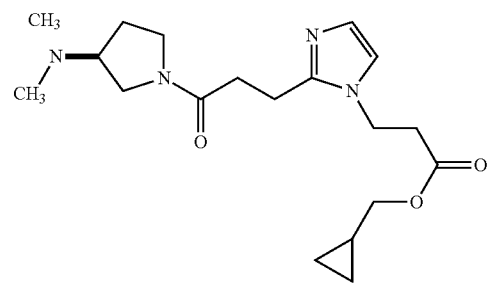 |
| 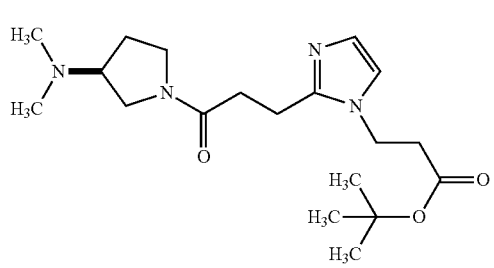 [SMILES: CN(C)[C@H]1CCN(C(=O)CCc2nccn2CCC(=O)OC(C)(C)C)C1] |

TABLE 1-1-continued
Structural formula
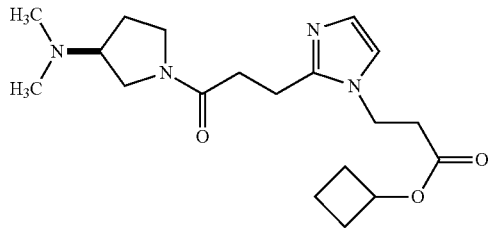 [SMILES: CN(C)[C@H]1CCN(C(=O)CCc2nccn2CCC(=O)OC2CCC2)C1]
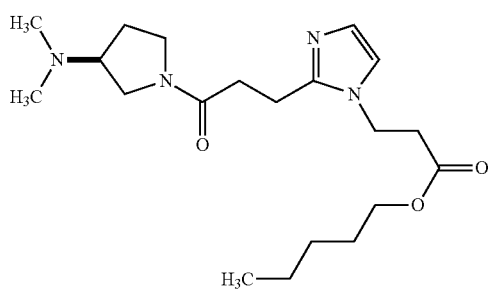 [SMILES: CCCCCOC(=O)CCn1ccnc1CCC(=O)N1CC[C@H](N(C)C)C1]
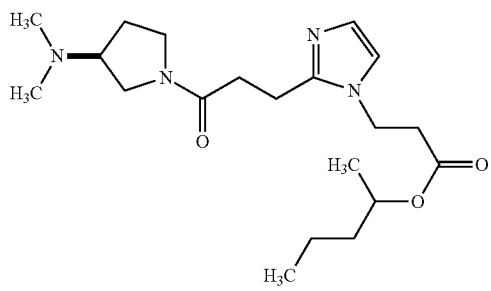 [SMILES: CCCC(C)OC(=O)CCn1ccnc1CCC(=O)N1CC[C@H](N(C)C)C1]
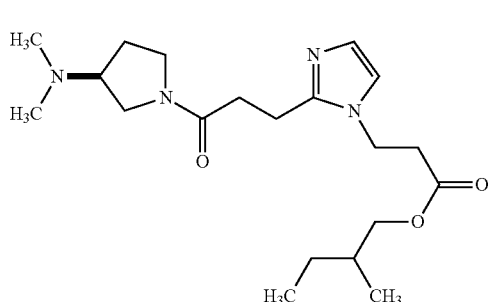
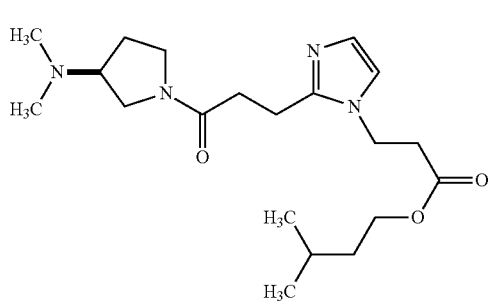 [SMILES: CC(C)CCOC(=O)CCn1ccnc1CCC(=O)N1CC[C@H](N(C)C)C1]
TABLE 1-1-continued
Structural formula
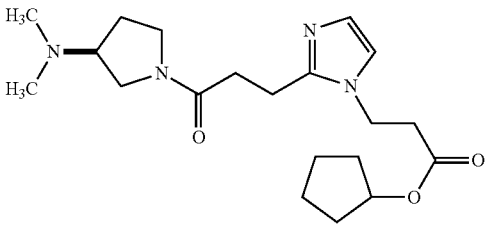 [SMILES: CN(C)[C@H]1CCN(C(=O)CCc2nccn2CCC(=O)OC2CCCC2)C1]
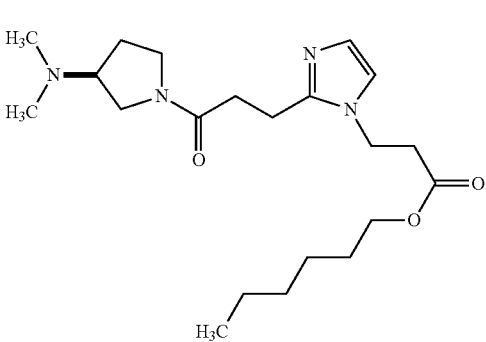 [SMILES: CCCCCCOC(=O)CCn1ccnc1CCC(=O)N1CC[C@H](N(C)C)C1]
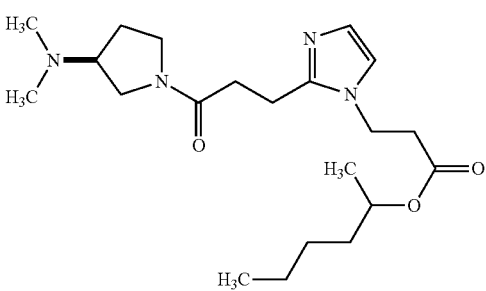 [SMILES: CCCCC(C)OC(=O)CCn1ccnc1CCC(=O)N1CC[C@H](N(C)C)C1]
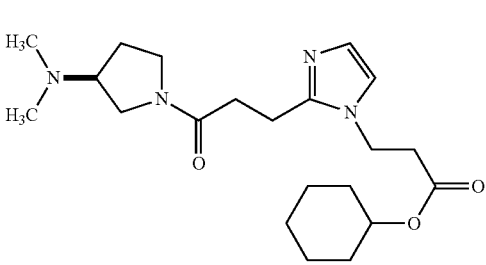 [SMILES: CN(C)[C@H]1CCN(C(=O)CCc2nccn2CCC(=O)OC2CCCCC2)C1]
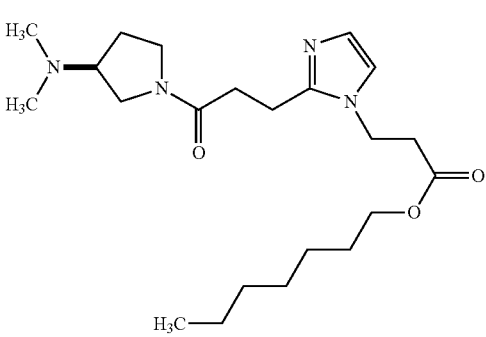 [SMILES: CCCCCCC(C)OC(=O)CCn1ccnc1CCC(=O)N1CC[C@H](N(C)C)C1]

TABLE 1-1-continued

Structural formula

TABLE 1-2

Structural formula

TABLE 1-2-continued

Structural formula

TABLE 1-2-continued
Structural formula
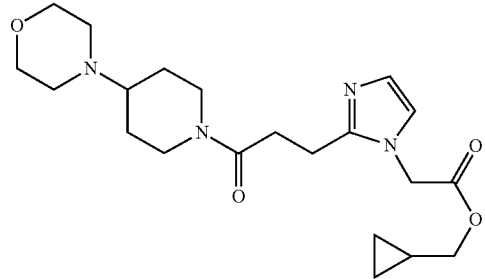 [SMILES: O=C(Cn1ccnc1CCC(=O)N1CCC(N2CCOCC2)CC1)OCC1CC1]
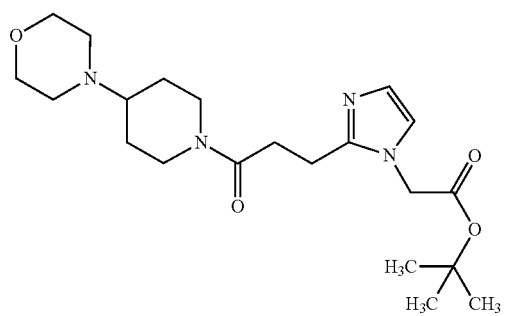 [SMILES: CC(C)(C)OC(=O)Cn1ccnc1CCC(=O)N1CCC(N2CCOCC2)CC1]
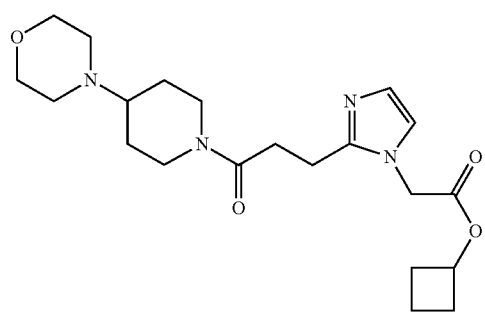 [SMILES: O=C(Cn1ccnc1CCC(=O)N1CCC(N2CCOCC2)CC1)OC1CCC1]
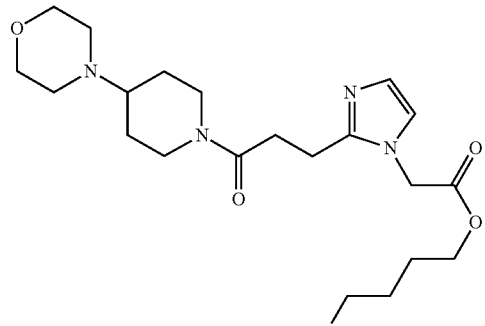
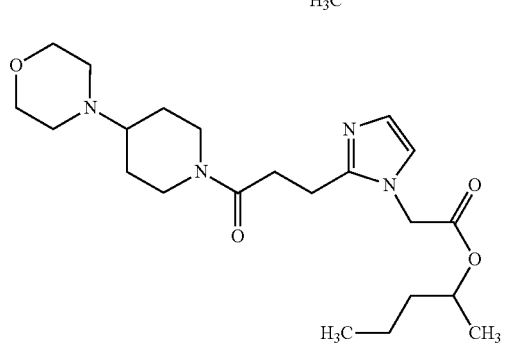
TABLE 1-2-continued
Structural formula
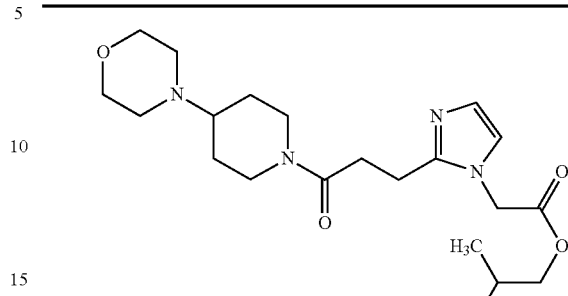
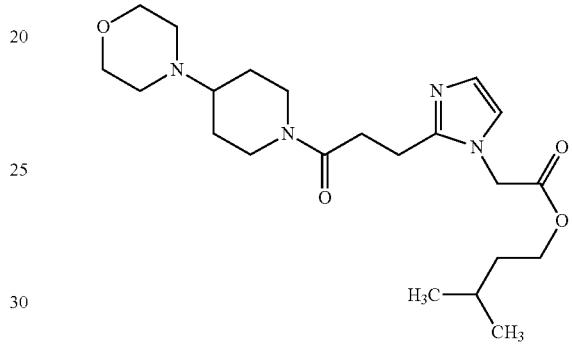
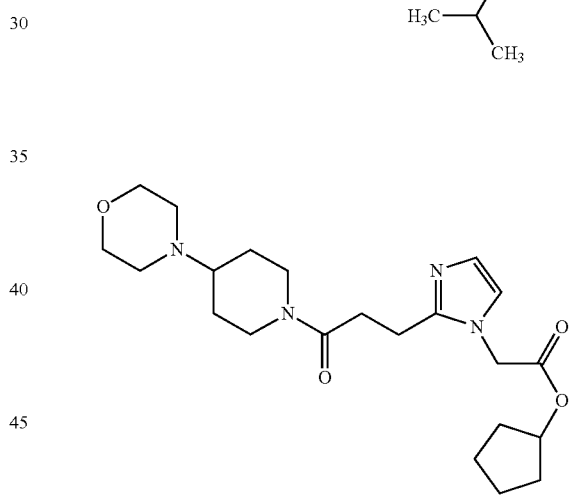
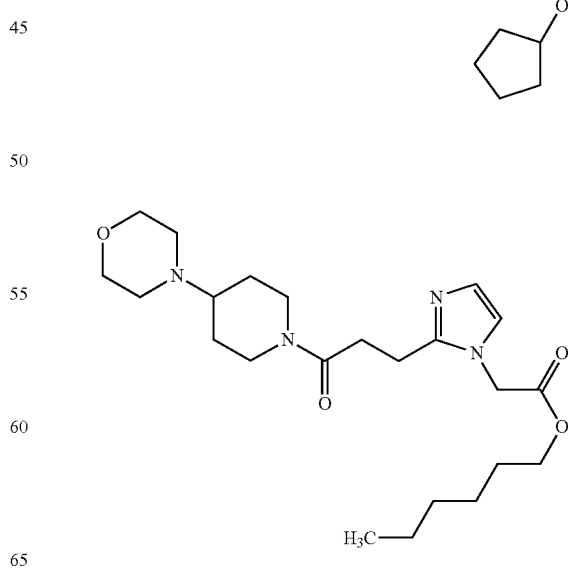

TABLE 1-2-continued

Structural formula

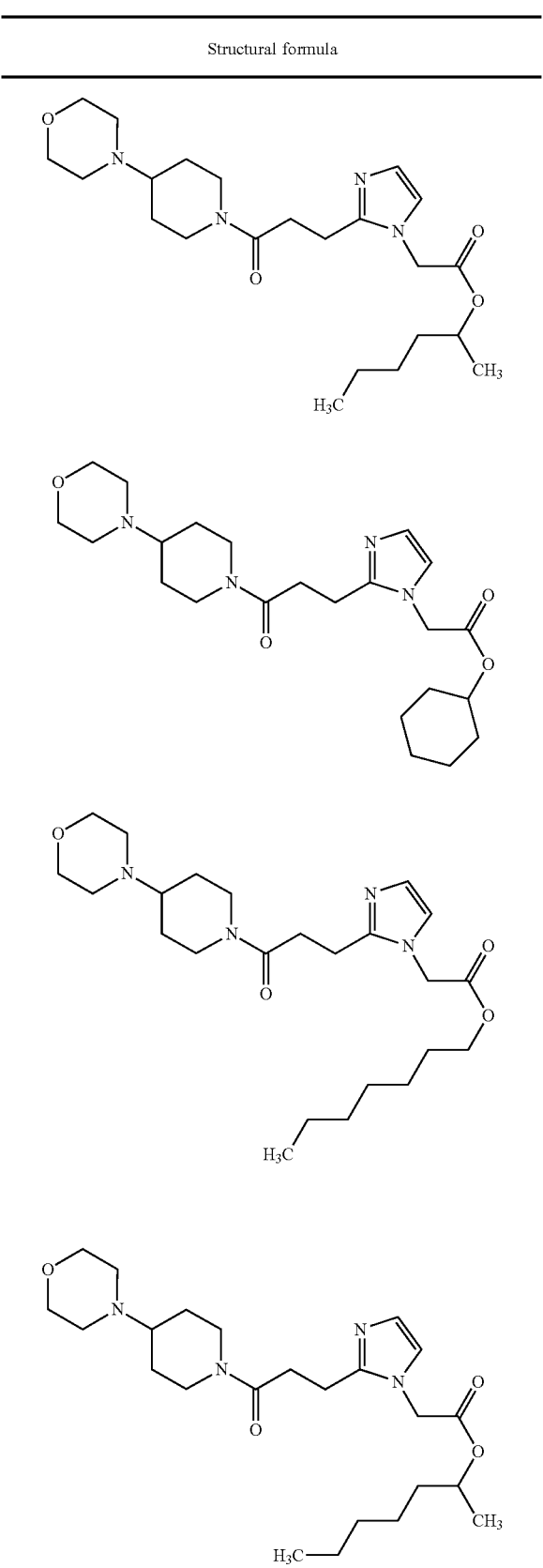

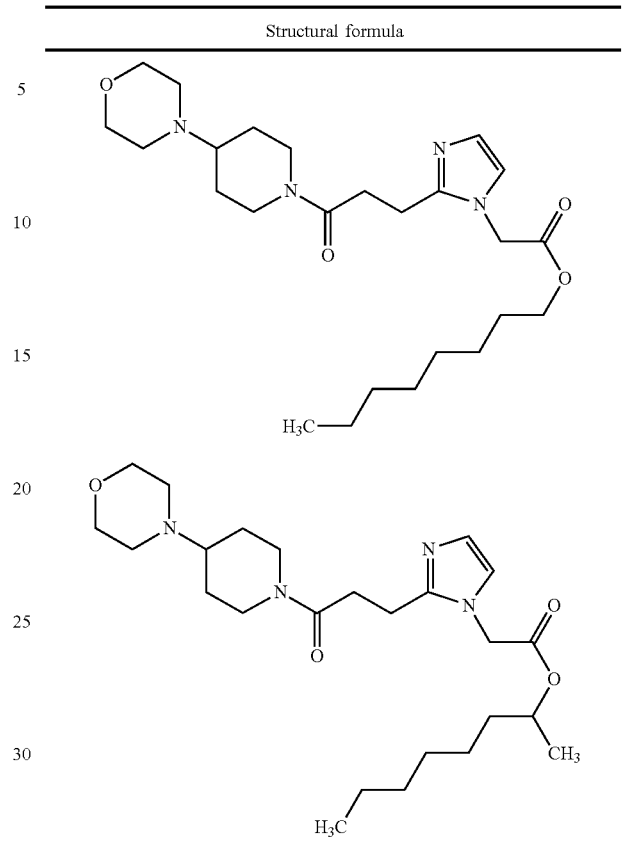

When the cyclic amine derivative (I) has isomers such as enantiomers and stereoisomers, any one of isomers and mixtures of them are included in the cyclic amine derivative (I). In addition, when conformational isomers are sometimes formed, such isomers and mixtures of these are included in the cyclic amine derivative (I). A desired isomer can be obtained by a known method or a similar method thereto. For example, when an enantiomer of a cyclic amine derivative (I) is present, the enantiomer separated from the cyclic amine derivative (I) is included in the cyclic amine derivative (I).

A desired enantiomer can be obtained by a known means (for example, an optically active synthetic intermediate is used or a final-product racemic mixture is subjected to a known method or a similar method thereto (for example, optical resolution)).

A cyclic amine derivative (I) may be labeled with an isotope. Examples of the radioisotope for use in labeling include $^2H$, $^3H$, $^{13}C$, $^{14}C$, $^{15}N$, $^{15}O$, $^{18}O$ and/or $^{125}I$.

As the pharmacologically acceptable salt of a cyclic amine derivative (I), for example, an inorganic salt such as a hydrochloride, a sulfate, a phosphate or a hydrobromide; or an organic salt such as an oxalate, a malonate, a citrate, a fumarate, a lactate, a malate, a succinate, a tartrate, an acetate, a trifluoroacetate, a maleate, a gluconate, a benzoate, a salicylate, a xinafoate, a pamoate, an ascorbate, an adipate, a methanesulfonate, a p-toluenesulfonate or a cinnamate. These salts may be present in the form of a hydrate, a solvate or a crystalline polymorph.

A cyclic amine derivative (I) can be synthesized by the production methods described below. The cyclic amine derivatives (I) obtained by the following production methods each can be isolated/purified by a known means (for example, solvent extraction, recrystallization and/or chromatography) and converted into desired salts by known methods or a similar method thereto. When a cyclic amine derivative (I) is obtained in the form of a salt, it can be converted into a cyclic amine derivative (I) or another desired salt by a known method or a similar method thereto.

In individual reactions of the production methods described below, when a starting compound has a hydroxyl group, an amino group or a carboxyl group, a protective group may be introduced in these groups. A desired compound can be obtained by removing the protective group if necessary after the reaction.

As the protective group of a hydroxyl group, for example, a trityl group, an aralkyl group having 7 to 10 carbon atoms (e.g., benzyl group) or a substituted silyl group (e.g., trimethylsilyl group, triethylsilyl group or tert-butyldimethylsilyl group) can be mentioned.

As the protective group of an amino group, for example, an alkylcarbonyl group having 2 to 6 carbon atoms (for example, acetyl group), a benzoyl group, an alkyloxycarbonyl group having 2 to 8 carbon atoms (for example, tert-butoxycarbonyl group or benzyloxycarbonyl group), an aralkyl group having 7 to 10 carbon atoms (for example, benzyl group) or a phthaloyl group can be mentioned.

As the protective group of a carboxyl group, for example, an alkyl group having 1 to 6 carbon atoms (e.g., methyl group, ethyl group or tert-butyl group) or an aralkyl group having 7 to 10 carbon atoms (for example, benzyl group) can be mentioned.

Removal of a protective group, which varies depending upon the type of protective group, can be performed in accordance with a known method (for example, Greene, T. W., "Greene's Protective Groups in Organic Synthesis," Wiley-Interscience) or a similar method thereto.

1-1. Production Method for Cyclic Amine Derivative (I):

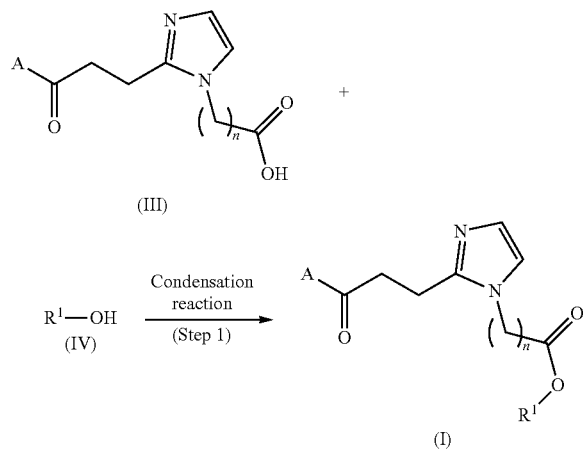

wherein individual reference symbols are the same as defined above.

Step 1

A cyclic amine derivative (I) can be obtained, for example, by the condensation reaction between a compound (III) and a compound (IV) by using a condensing agent in the presence or absence of a base.

As the compound (III) and compound (IV) to be used in the condensation reaction, commercially available compounds can be directly used. However, they can be synthesized, for example, in accordance with the production methods that will be described below.

As the base to be used in the condensation reaction, for example, an aromatic amine such as pyridine or lutidine; or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mol of a compound (III) and more preferably 0.8 to 5 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphorylazide (DPPA), 4-(4,6-dimethoxy-1,3,5-triazin-2-yl)-4-methylmorpholinium chloride (DMTMM), isobutyl chloroformate, diethylacetyl chloride or trimethylacetyl chloride can be mentioned. These condensing agents are used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (III) and more preferably 0.8 to 5 moles.

The amount of the compound (IV) to be used in the condensation reaction is preferably 0.5 to 5 moles relative to 1 mole of a compound (III) and more preferably 0.8 to 2 moles.

The condensation reaction is generally performed in a solvent. The solvent which does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; an amide such as N,N-dimethylformamide or N-methylpyrrolidone; an alcohol such as methanol, ethanol or 2-propanol; or an aliphatic nitrile such as acetonitrile or propionitrile can be mentioned. A mixed solvent of these may be used. When an aromatic amine such as pyridine is selected as the solvent, a condensation reaction can be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 60 hours.

1-2. Salt Formation Steps of Cyclic Amine Derivative (I):

Pharmacologically acceptable salts of a cyclic amine derivative (I) can be obtained, for example, through a salt formation reaction performed by mixing the cyclic amine derivative (I) and an acid.

As the acid to be used for a salt formation reaction, for example, an inorganic acid such as hydrochloric acid, sulfuric acid, phosphoric acid or hydrobromic acid; and an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluenesulfonic acid or cinnamic acid can be mentioned.

A salt formation reaction is generally performed in a solvent. The solvent that does not inhibit the reaction is appropriately selected. As the solvent, for example, an aliphatic alcohol such as methanol, ethanol or isopropanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

2. Production Method for Compound (III):

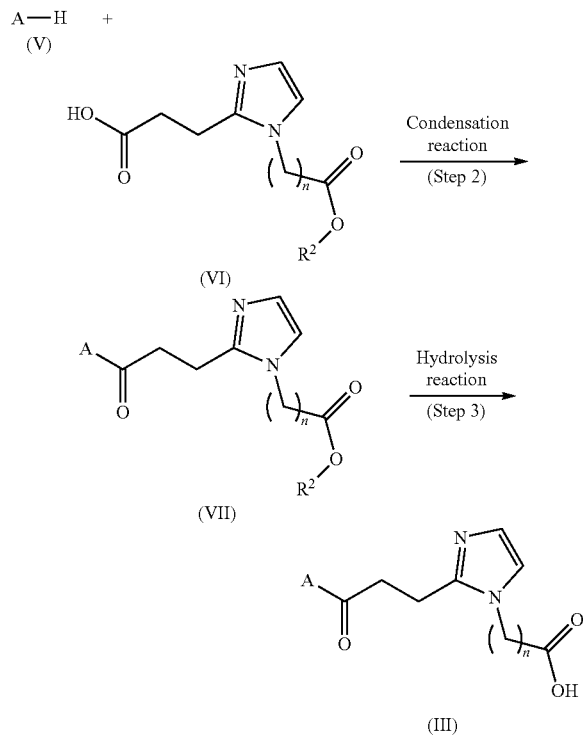

wherein $R^2$ represents an alkyl group having 1 to 6 carbon atoms such as a methyl group, an ethyl group, a n-propyl group or a n-butyl group. Other reference symbols are the same as defined above.

Step 2

A compound (VII) can be obtained by the condensation reaction of a compound (V) and a compound (VI) with a condensing agent in the presence or absence of a base.

In the condensation reaction, the compound (V) and a salt thereof can be used. As the salt herein, for example, the same salt as a pharmacologically acceptable salt as mentioned above can be mentioned.

As the compound (V) and compound (VI) to be used in the condensation reaction, commercially available compounds can be directly used. However, they can be synthesized, for example, in accordance with the production methods that will be described below.

As the base to be used in the condensation reaction, for example, an aromatic amine such as pyridine or lutidine; or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mole of a compound (V) and more preferably 0.8 to 5 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphorylazide (DPPA), 4-(4,6-dimethoxy-1,3,5-triazin-2-yl)-4-methylmorpholinium chloride (DMTMM), isobutyl chloroformate, diethylacetyl chloride or trimethylacetyl chloride can be mentioned. These condensing agents are used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (V) and more preferably 0.8 to 5 moles.

The amount of the compound (VI) to be used in the condensation reaction is preferably 0.5 to 3 moles relative to 1 mole of a compound (V) and more preferably 0.8 to 1.5 moles.

The condensation reaction is generally performed in a solvent. The solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; an amide such as N,N-dimethylformamide or N-methylpyrrolidone; an alcohol such as methanol, ethanol or 2-propanol; or an aliphatic nitrile such as acetonitrile or propionitrile can be mentioned. A mixed solvent of these may be used. When an aromatic amine such as pyridine is selected as the solvent, a condensation reaction can be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 60 hours.

Step 3

A compound (III) can be obtained by the hydrolysis reaction of a compound (VII) in the presence of a base.

As the base to be used in the hydrolysis reaction, for example, lithium hydroxide, potassium hydroxide or sodium hydroxide can be mentioned.

The amount of the base to be used in the hydrolysis reaction is preferably 0.5 to 3 moles relative to 1 mole of a compound (VII) and more preferably 0.8 to 2 moles.

The hydrolysis reaction is generally performed in a solvent. The solvent that does not inhibit the reaction is appropriately selected. As the solvent, for example, an aliphatic alcohol such as methanol, ethanol or propanol; or water can be mentioned. A mixture of these solvents may be used.

In the hydrolysis reaction, the reaction temperature is preferably, −20° C. to 150° C. and more preferably 0 to 100° C.

In the hydrolysis reaction, the reaction time, which varies depending upon the reaction conditions, is preferably 5 minutes to 72 hours, and more preferably 30 minutes to 48 hours.

3. Production Method for Compound (VI):

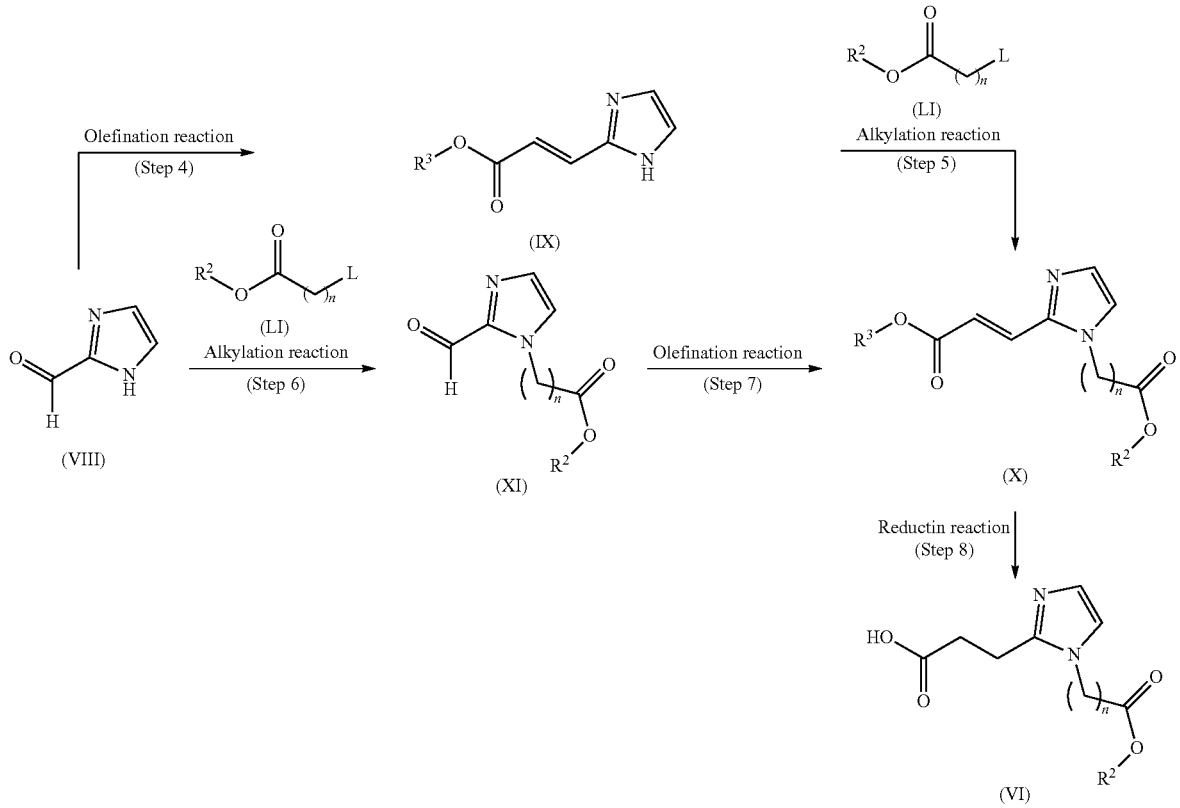

wherein L represents a leaving group such as a chlorine atom, a bromine atom or an iodine atom, R³ represents an aralkyl group having 7 to 10 carbon atoms such as a benzyl group, and other reference symbols are the same as defined above.

Step 4

A compound (IX) can be obtained by an olefination reaction of a compound (VIII) with an olefination reagent in the presence or absence of a base.

As the compound (VIII) to be used in the olefination reaction, a commercially available compound can be used.

As the base to be used in the olefination reaction, for example, sodium hydride can be mentioned.

The amount of the base to be used in the olefination reaction is preferably 0.5 to 10 moles relative to 1 mole of the compound (VIII) and more preferably 0.8 to 5 moles.

As the olefination reagent to be used in the olefination reaction, for example, a Horner-Emmons reagent such as benzyl dimethyl phosphonoacetate; or a Wittig reagent such as benzyl 2-(triphenylphosphoranylidene)acetate can be mentioned. As the Horner-Emmons reagent or Wittig reagent, a commercially available compound can be directly used.

The amount of the olefination reagent to be used in the olefination reaction is preferably 0.5 to 3 moles relative to 1 mole of a compound (VIII) and more preferably 0.8 to 2 moles.

The olefination reaction is generally performed in a solvent. The solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 5

A compound (X) can be obtained by deprotonation of a compound (IX) with a base, followed by an alkylation reaction with an alkylating reagent (LI).

As the base to be used in the alkylation reaction, for example, a metal carbonate such as sodium carbonate, potassium carbonate or cesium carbonate; an alkali metal hydride such as sodium hydride or potassium hydride; or a butyllithium such as n-butyllithium, sec-butyllithium or tert-butyllithium can be mentioned.

The amount of the base to be used in the alkylation reaction is preferably 0.5 to 3 moles relative to 1 mole of a compound (IX) and more preferably 0.8 to 2 moles.

The amount of the alkylating reagent (LI) to be used in the alkylation reaction is preferably 0.5 to 3 moles relative to 1 mole of a compound (IX) and more preferably 0.8 to 2 moles.

The alkylation reaction is generally performed in a solvent. The solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the alkylation reaction, the reaction temperature is preferably, −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 6

A compound (XI) can be obtained by deprotonation of a compound (VIII) with a base, followed by an alkylation reaction with an alkylating reagent (LI).

As the base to be used in the alkylation reaction, for example, a metal carbonate such as sodium carbonate, potassium carbonate or cesium carbonate; an alkali metal hydride such as sodium hydride or potassium hydride; or a butyllithium such as n-butyllithium, sec-butyllithium or tert-butyllithium can be mentioned.

The amount of the base to be used in the alkylation reaction is preferably 0.5 to 3 moles relative to 1 mole of a compound (VIII) and more preferably 0.8 to 2 moles.

As the alkylating reagent (LI) to be used in the alkylation reaction, a commercially available product can be used.

The amount of the alkylating reagent (LI) to be used in the alkylation reaction is preferably 0.5 to 10 moles relative to 1 mole of a compound (VIII) and more preferably 0.8 to 5 moles.

The alkylation reaction is generally performed in a solvent. The solvent that does not inhibit the reaction is appropriately selected. As the solvent, for example, an aliphatic hydrocarbon such as heptane or hexane; or an ether such as tetrahydrofuran, diethyl ether or 1,4-dioxane can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 7

A compound (X) can be obtained by an olefination reaction of a compound (XI) with an olefination reagent in the presence or absence of a base.

As the base to be used in the olefination reaction, for example, sodium hydride can be mentioned.

The amount of the base to be used in the olefination reaction is preferably 0.5 to 10 moles relative to 1 mole of the compound (XI) and more preferably 0.8 to 5 moles.

As the olefination reagent to be used in the olefination reaction, for example, a Horner-Emmons reagent such as benzyl dimethyl phosphonoacetate; or a Wittig reagent such as benzyl 2-(triphenylphosphoranylidene)acetate can be mentioned. As the Horner-Emmons reagent or Wittig reagent, a commercially available compound can be directly used.

The amount of the olefination reagent to be used in the olefination reaction, is preferably 0.5 to 3 moles relative to 1 mole of a compound (XI) and more preferably 0.8 to 2 moles.

The olefination reaction is generally performed in a solvent. The solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 8

A compound (VI) can be obtained by the reduction reaction of a compound (X) in the presence of a transition metal catalyst under a hydrogen atmosphere.

As the transition metal catalyst to be used in the reduction reaction, for example, palladium-carbon can be mentioned.

The amount of the transition metal catalyst to be used in the reduction reaction is preferably 0.1 to 100 wt % relative to a compound (X) and more preferably 1 to 50 wt %.

The reduction reaction is generally performed in a solvent. The solvent that does not inhibit the reaction is appropriately selected. As the solvent, for example, an aliphatic hydrocarbon such as heptane or hexane; or an aliphatic alcohol such as methanol, ethanol or propanol can be mentioned. A mixture of these solvents may be used.

In the reduction reaction, the reaction temperature is preferably 0 to 80° C. and more preferably 10 to 40° C.

In the reduction reaction, the reaction time, which varies depending upon the reaction conditions, is preferably 5 minutes to 72 hours, and more preferably 30 minutes to 48 hours.

4. Production Method for a Compound (Va):

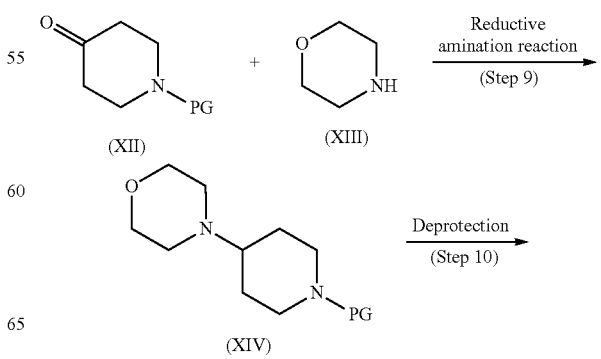

-continued

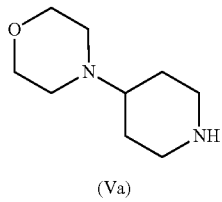

(Va)

wherein PG represents a protective group; and other reference symbols are the same as defined above.

Step 9

A compound (XIV) can be obtained by the reductive amination reaction between a compound (XII) and a compound (XIII).

As the compound (XII) and a compound (XIII) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 10

A compound (V) wherein A represents a group represented by the general formula (IIb), i.e., a compound (Va), can be obtained by deprotection of a compound (XIV).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

The analgesic action of a cyclic amine derivative (I) or a pharmacologically acceptable salt thereof, particularly the therapeutic effect on neuropathic pain and fibromyalgia syndrome can be evaluated by use of an appropriate animal model. As the appropriate animal model for neuropathic pain, for example, a mouse or rat partial sciatic nerve ligation model (Malmberg et al., Pain, vol. 76, p. 215-222, 1998) or a mouse or rat spinal nerve ligation model (Kim et al., Pain, vol. 50, p. 355-363, 1992) can be mentioned. As the appropriate animal model for fibromyalgia syndrome, for example, rat fibromyalgia syndrome models (Sluka et al., Journal of Pharmacology and Experimental Therapeutics, vol. 302, p. 1146-1150, 2002; Nagakura et al., Pain, vol. 146, p. 26-33, 2009; Sluka et al., Pain, vol. 146, p. 3-4, 2009) can be mentioned.

The cyclic amine derivative (I) or a pharmacologically acceptable salt thereof, since it has an excellent analgesic action, particularly a therapeutic effect on neuropathic pain and/or fibromyalgia syndrome, can be used as a medicine, preferably used as an analgesic agent, and particularly preferably as a therapeutic agent for neuropathic pain and/or fibromyalgia syndrome.

The cyclic amine derivative (I) or a pharmacologically acceptable salt thereof can be administered for prolonged periods in treating neuropathic pain and/or fibromyalgia syndrome because central nervous system adverse effects can be expectedly reduced.

As the neuropathic pain herein, for example, cancer pain, shingles pain, postherpetic neuralgia, AIDS-related neuralgia, painful diabetic neuropathy or trigeminal neuralgia can be mentioned.

The "fibromyalgia syndrome" is a symptom diagnosed by a specialist physician as fibromyalgia syndrome. The diagnosis by a specialist physician is generally made with reference to the classification standard of the American College of Rheumatology.

The cyclic amine derivative (I) or a pharmacologically acceptable salt thereof is also useful for treating acute and chronic pain. The acute pain usually lasts for a short period, and, for example, postoperative pain, pain after tooth extraction or trigeminal neuralgia can be mentioned. The chronic pain is defined as pain usually lasting for 3 to 6 months and includes somatogenic pain and psychogenic pain, and, for example, chronic rheumatoid arthritis, osteoarthritis or postherpetic neuralgia can be mentioned.

A medicine containing a cyclic amine derivative (I) or a pharmacologically acceptable salt as an active ingredient, exerts an excellent analgesic action, particularly a therapeutic effect on neuropathic pain and/or fibromyalgia syndrome when it is administered to a mammal (for example, mouse, rat, hamster, rabbit, cat, dog, cow, sheep, monkey or human), especially to a human.

When a cyclic amine derivative (I) or a pharmacologically acceptable salt thereof is used as a medicine, the cyclic amine derivative (I) or a pharmacologically acceptable salt thereof directly or in combination with a pharmaceutically acceptable carrier can be orally or parenterally administered.

As the dosage form when a medicine containing a cyclic amine derivative (I) or a pharmacologically acceptable salt thereof as an active ingredient is orally administered, for example, tablets (including sugar-coated and film-coated tablets), pills, granules, powders, capsules (including soft capsules and micro capsules), syrups, emulsions or suspensions can be mentioned. As the dosage form when a medicine containing a cyclic amine derivative (I) or a pharmacologically acceptable salt thereof as an active ingredient is parenterally administered, for example, injections, infusions, drops, suppositories, endermic liniments or adhesive patches can be mentioned. It is further effective to prepare a sustained-release formulation by using an appropriate base (for example, a butyric acid polymer, a glycolic acid polymer, a butyric acid-glycolic acid copolymer, mixtures of a butyric acid polymer and a glycolic acid polymer, or a polyglycerol fatty acid ester) in combination.

Formulations having the aforementioned dosage forms can be prepared in accordance with production methods known in the field of drug formulation. In this case, if necessary, production can be made by adding an excipient, a binder, a lubricant, a disintegrating agent, a sweetening agent, a surfactant, a suspending agent or an emulsifying agent, which is generally used in the field of drug formulation.

Tablets can be prepared, for example, by adding an excipient, a binder, a disintegrating agent or a lubricant. Pills and granules can be prepared by adding, for example, an excipient, a binder or a disintegrating agent. Powders and capsules can be prepared by adding, for example, an excipient. Syrups can be prepared by adding, for example, a sweetening agent. Emulsions or suspensions can be prepared by adding, for example, a surfactant, a suspending agent or an emulsifier.

As the excipient, for example, lactose, glucose, starch, sucrose, microcrystalline cellulose, powdered glycyrrhiza, mannitol, sodium hydrogen carbonate, calcium phosphate or calcium sulfate can be mentioned.

As the binder, for example, a starch paste solution, a gum arabic solution, a gelatin solution, a tragacanth solution, a carboxymethylcellulose solution, a sodium alginate solution or glycerin can be mentioned.

As the disintegrating agent, for example, starch or calcium carbonate can be mentioned.

As the lubricant, for example, magnesium stearate, stearic acid, calcium stearate or purified talc can be mentioned.

As the sweetening agent, for example, glucose, fructose, invert sugar, sorbitol, xylitol, glycerin or simple syrup can be mentioned.

As the surfactant, for example, sodium lauryl sulfate, polysorbate 80, sorbitan monofatty acid ester or stearic acid polyoxyl 40 can be mentioned.

As the suspending agent, for example, Gum arabic, sodium alginate, sodium carboxymethylcellulose, methyl cellulose or bentonite can be mentioned.

As the emulsifier, for example, Gum arabic, tragacanth, gelatin or polysorbate 80 can be mentioned.

When a medicine containing a cyclic amine derivative (I) or a pharmacologically acceptable salt thereof as an active ingredient is prepared in the aforementioned dosage forms, a coloring agent, a preserving agent, a fragrance, a flavoring agent, a stabilizer or a thickener generally used in the field of drug formulation can be added.

The dose per day of a medicine containing a cyclic amine derivative (I) or a pharmacologically acceptable salt thereof as an active ingredient varies depending upon e.g., the state or body weight of the patient or the type or administration route of a compound. For example, in oral administration to an adult (weight: about 60 kg), the amount of the cyclic amine derivative (I) or a pharmacologically acceptable salt thereof serving as an active ingredient is 1 to 1000 mg and administration is preferably made in 1 to 3 divided doses. For example, in parenteral administration to an adult (weight: about 60 kg) by an injectable solution, the amount of the cyclic amine derivative (I) or a pharmacologically acceptable salt thereof serving as an active ingredient in e.g., an injection, is 0.01 to 100 mg per body weight (1 kg). The injectable solution is preferably intravenously administered. As the cyclic amine derivative (I) or a pharmacologically acceptable salt thereof has excellent oral absorbability, it is particularly preferably administered orally.

A cyclic amine derivative (I) or a pharmacologically acceptable salt thereof may be used in combination with other medicinal agents in an appropriate blending ratio to supplement or enhance a therapeutic or prophylactic effect or reduce the dose. In this case, as the other medicinal agents, for example, an antidepressant such as amitriptyline, milnacipran or duloxetine; an anxiolytic such as alprazolam; an anticonvulsant such as carbamazepine; a local anesthetic such as lidocaine; a sympathetic agonist such as adrenaline; an NMDA receptor antagonist such as ketamine; a GABA transaminase inhibitor such as sodium valproate; a calcium channel blocker such as pregabalin; a serotonin receptor antagonist such as risperidone; a GABA receptor function enhancer such as diazepam; or an anti-inflammatory drug such as diclofenac can be mentioned.

EXAMPLES

Our derivatives, agents, medicines and methods will be described in detail below with reference to Examples and Reference Examples. However, this disclosure is not limited to them.

In the following description, the names of the solvents shown in the NMR data represent the solvents used in the measurement. The 400 MHz NMR spectra were measured by using JNM-AL 400 series Nuclear Magnetic Resonance (NMR) spectrometer (JEOL, Ltd.). Chemical shifts are expressed by δ (unit: ppm) using tetramethylsilane as the reference, and the respective signals, respectively have the following meanings: s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), and tt (triple triplet). The ESI-MS spectra were measured by using Agilent Technologies 1200 Series, G6130A (from Agilent Technology). Commercially available products were used for all the solvents. For flash column chromatography, YFLC W-prep2XY (from YAMAZEN) was used.

Raw materials and intermediates of cyclic amine derivatives (I) were synthesized by the methods described in the following Reference Examples. Note that commercially-available products were used for the compounds used in synthesizing the compounds of Reference Examples for which synthesis methods are not described below.

Reference Example 1: Synthesis of (E)-benzyl 3-(1H-imidazol-2-yl)acrylate

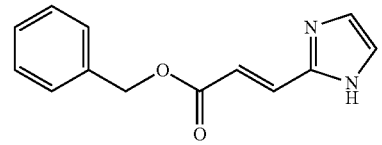 [SMILES: O=C(/C=C/c1ncc[nH]1)OCc1ccccc1]

Benzyl dimethylphosphonoacetate (5.12 mL, 24.4 mmol) was added to a suspension of sodium hydride (55%, 1.12 g, 25.6 mmol) in tetrahydrofuran (40.0 mL) at 0° C., and the reaction liquid was stirred at the same temperature for 1 hour. 1H-Imidazole-2-carbaldehyde (2.46 g, 25.6 mmol) was added to the reaction liquid at 0° C., and the reaction liquid was stirred at room temperature for 60 hours. A saturated aqueous solution of ammonium chloride was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash column chromatography (silica gel, chloroform/methanol) to obtain (E)-benzyl 3-(1H-imidazol-2-yl)acrylate (0.380 g, 1.66 mmol, 7%) as a white solid.

$^1$H-NMR (400 MHz, CDCl$_3$) δ: 5.25 (2H, s), 6.62 (1H, d, J=15.6 Hz), 7.14-7.23 (2H, m), 7.28-7.43 (5H, m), 7.57 (1H, d, J=16.0 Hz).

ESI-MS: m/z=229 (M+H)$^+$.

Reference Example 2: Synthesis of (E)-benzyl 3-(1-(3-ethoxy-3-oxopropyl)-1H-imidazol-2-yl)acrylate

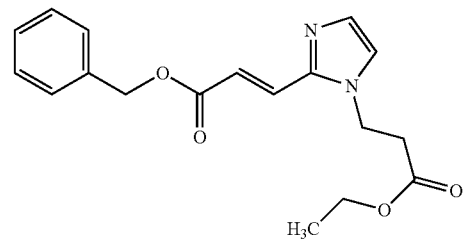 [SMILES: CCOC(=O)CCn1ccnc1/C=C/C(=O)OCc1ccccc1]

Potassium carbonate (0.606 g, 4.38 mmol), ethyl 3-bromopropanoate (0.419 mL, 3.29 mmol), and potassium iodide (0.364 g, 2.19 mmol) were added to a solution of (E)-benzyl 3-(1H-imidazol-2-yl)acrylate (0.500 g, 2.19 mmol) in N,N-dimethylformamide (7.3 mL) at room temperature, the temperature of the reaction liquid was raised to 90° C., and the reaction liquid was stirred for 4 hours. Distilled water was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash column chromatography (silica gel, n-hexane/ethyl acetate) to obtain (E)-benzyl 3-(1-(3-ethoxy-3-oxopropyl)-1H-imidazol-2-yl)acrylate (0.520 g, 1.59 mmol, 72%) as a yellow oil.

$^1$H-NMR (400 MHz, CDCl$_3$) δ: 1.23 (3H, t, J=7.2 Hz), 2.76 (2H, t, J=7.2 Hz), 4.13 (2H, q, J=7.2 Hz), 4.35 (2H, t, J=7.2 Hz), 5.26 (2H, s), 6.91 (1H, d, J=15.6 Hz), 7.06 (1H, brs), 7.15 (1H, brs), 7.30-7.42 (5H, m), 7.55 (1H, d, J=15.6 Hz).

ESI-MS: m/z=329 (M+H)$^+$.

Reference Example 3: Synthesis of crude 3-(1-(3-ethoxy-3-oxopropyl)-1H-imidazol-2-yl)propanoic acid

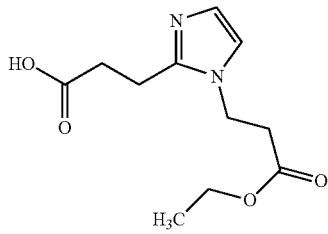 [SMILES: CCOC(=O)CCn1ccnc1CCC(=O)O]

Palladium-carbon (10% wet, 0.169 g, 0.159 mmol) was added to a solution of (E)-benzyl 3-(1-(3-ethoxy-3-oxopropyl)-1H-imidazol-2-yl)acrylate (0.520 g, 1.59 mmol) in ethanol (9.0 mL) at room temperature, and the reaction liquid was stirred under hydrogen atmosphere at the same temperature for 16 hours. The reaction liquid was filtered through Celite, and the filtrate was concentrated under reduced pressure to obtain a crude product of 3-(1-(3-ethoxy-3-oxopropyl)-1H-imidazol-2-yl)propanoic acid.

Reference Example 4: Synthesis of ethyl (S)-3-(2-(3-(3-(dimethylamino)pyrrolidin-1-yl)-3-oxopropyl)-1H-imidazol-1-yl)propanoate

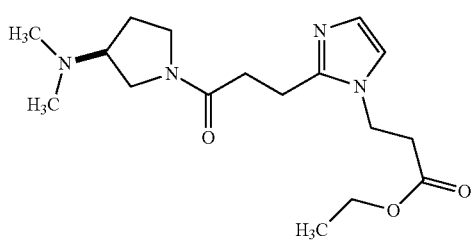 [SMILES: CCOC(=O)CCn1ccnc1CCC(=O)N1CC[C@H](N(C)C)C1]

Diisopropylethylamine (0.0870 mL, 0.499 mmol), HBTU (0.152 g, 0.400 mmol) and (S)-3-(dimethylamino)pyrrolidine (0.0420 mL, 0.333 mmol) were added to a solution of crude 3-(1-(3-ethoxy-3-oxopropyl)-1H-imidazol-2-yl)propanoic acid (0.0800 g, 0.333 mmol) in dichloromethane (1.6 mL) at room temperature, and the reaction liquid was stirred at the same temperature for 5 hours. The reaction liquid was concentrated under reduced pressure. The residue was purified by flash column chromatography (NH silica gel, chloroform/methanol) to obtain ethyl (S)-3-(2-(3-(3-(dimethylamino)pyrrolidin-1-yl)-3-oxopropyl)-1H-imidazol-1-yl)propanoate (0.103 g, 0.306 mmol, 92%) as a reddish brown oil.

$^1$H-NMR (400 MHz, CDCl$_3$) δ: 1.23-1.27 (3H, m), 1.67-1.91 (1H, m), 2.06-2.26 (7H, m), 2.58-3.36 (9H, m), 3.43-3.83 (2H, m), 4.12-4.28 (4H, m), 6.85-6.93 (2H, m).

ESI-MS: m/z=337 (M+H)$^+$.

Reference Example 5: Synthesis of (S)-3-(2-(3-(3-(dimethylamino)pyrrolidin-1-yl)-3-oxopropyl)-1H-imidazol-1-yl)propanoic acid

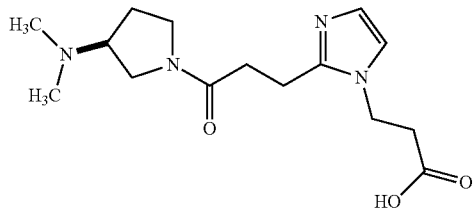 [SMILES: CN(C)[C@H]1CCN(C(=O)CCc2nccn2CCC(=O)O)C1]

An aqueous solution of sodium hydroxide (1.0 N, 0.948 mL, 0.948 mmol) was added to a solution of ethyl (S)-3-(2-(3-(3-(dimethylamino)pyrrolidin-1-yl)-3-oxopropyl)-1H-imidazol-1-yl)propanoate (0.290 g, 0.862 mmol) in ethanol (1.0 mL) at room temperature. The reaction liquid was stirred at the same temperature for 2 hours and cooled to 0° C. After hydrochloric acid (1.0 N) was added to the reaction liquid to neutralize it, the reaction liquid was concentrated under reduced pressure and subjected to azeotropic distillation with toluene, and ethanol was added to the reaction liquid. The resulting precipitate was filtered through Celite and the filtrate was concentrated under reduced pressure to obtain (S)-3-(2-(3-(3-(dimethylamino)pyrrolidin-1-yl)-3-oxopropyl)-1H-imidazol-1-yl)propanoate (0.220 g, 0.713 mmol, 83%) as a white solid.

$^1$H-NMR (400 MHz, CD$_3$OD) δ: 1.95-2.50 (3H, m), 2.74-3.10 (11H, m), 3.54-4.46 (7H, m), 7.27-7.32 (1H, m), 7.42-7.46 (1H, m).

ESI-MS: 309 (M+H)$^+$.

Reference Example 6: Synthesis of 4-(piperidin-4-yl) morpholin

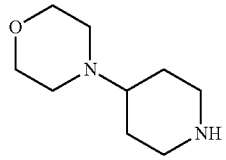 [SMILES: C1CC(N2CCOCC2)CCN1]

Morpholin (0.792 g, 9.09 mmol), sodium triacetoxyborohydride (1.93 g, 9.09 mmol), acetic acid (0.0460 g, 0.758 mmol) were added to a solution of 1-tert-butoxycarbonyl- 4-piperidinone (1.51 g, 7.58 mmol) in dichloromethane (25.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. 4-(Piperidin-4-yl) morpholin (1.52 g, 5.63 mmol, 74%) was obtained as a yellow solid.

$^1$H-NMR (400 MHz, CDCl$_3$) δ: 1.34 (2H, dd, J=12.0, 4.0 Hz), 1.40 (2H, dd, J=12.0, 4.0 Hz), 1.85 (2H, d, J=12.4 Hz), 2.28 (1H, tt, J=11.2, 4.0 Hz), 3.53-3.63 (6H, m), 3.15 (2H, d, J=12.4 Hz), 3.73 (4H, t, J=4.4 Hz).

ESI-MS: m/z=171 (M+H)$^+$

Reference Example 7: Synthesis of ethyl 2-(2-formyl-1H-imidazol-1-yl)acetate

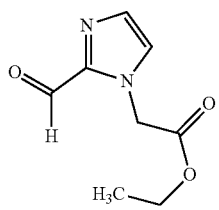

Potassium carbonate (1.44 g, 10.4 mmol), ethyl chloroacetate (0.585 mL, 5.46 mmol) and potassium iodide (0.864 g, 5.20 mmol) were added to a solution of 1H-imidazole-2-carbaldehyde (0.500 g, 5.20 mmol) in N,N-dimethyl formamide (10.0 mL) at room temperature. The temperature of the reaction liquid was increased to 90° C. and the reaction liquid was stirred for 4 hours. Distilled water was added to the reaction liquid and extracted with ethyl acetate. The organic layer was washed with a 10% aqueous solution of sodium chloride, dried over anhydrous sodium sulfate and filtered. The filtrate was concentrated under reduced pressure. The residue was purified by flash column chromatography (silica gel, chloroform/methanol) to obtain ethyl 2-(2-formyl-1H-imidazol-1-yl)acetate (0.269 g, 1.48 mmol, 28%) as a yellow oil.

$^1$H-NMR (400 MHz, CDCl$_3$) δ: 1.29 (3H, t, J=7.2 Hz), 4.25 (2H, q, J=7.2 Hz), 5.14 (2H, s), 7.15 (1H, brs), 7.33 (1H, s), 9.79-9.91 (1H, m).

ESI-MS: m/z=183 (M+H)$^+$.

Reference Example 8: Synthesis of (E)-benzyl 3-(1-(2-ethoxy-2-oxoethyl)-1H-imidazol-2-yl)acrylate

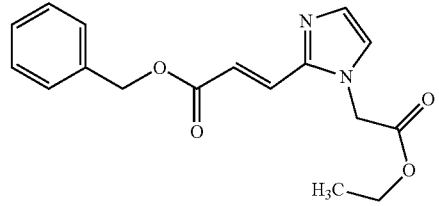 [SMILES: CCOC(=O)Cn1ccnc1/C=C/C(=O)OCc1ccccc1]

Benzyl dimethyl phosphonoacetate (4.61 mL, 22.0 mmol) was added to a suspension solution of sodium hydride (55%, 0.958 g, 22.0 mmol) in tetrahydrofuran (30.0 mL) at 0° C. The reaction liquid was stirred at the same temperature for 1 hour. Ethyl 2-(2-formyl-1H-imidazol-1-yl)acetate (4.00 g, 22.0 mmol) was added to the reaction liquid at 0° C. The reaction liquid was stirred at room temperature for 3 hours. A saturated aqueous solution of ammonium chloride was added to the reaction liquid and the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by flash column chromatography (silica gel, n-hexane/ethyl acetate) to obtain (E)-benzyl 3-(1-(2-ethoxy-2-oxoethyl)-1H-imidazol-2-yl)acrylate (4.31 g, 13.7 mmol, 62%) as a white solid.

$^1$H-NMR (400 MHz, CDCl$_3$) δ: 1.28 (3H, t, J=7.2 Hz), 4.24 (2H, q, J=7.2 Hz), 4.77 (2H, s), 5.25 (2H, s), 6.92 (1H, d, J=15.6 Hz), 7.02 (1H, brs), 7.21 (1H, brs), 7.28-7.45 (6H, m).

ESI-MS: m/z=315 (M+H)$^+$.

Reference Example 9: Synthesis of crude 3-(1-(2-ethoxy-2-oxoethyl)-1H-imidazol-2-yl)propanoic acid

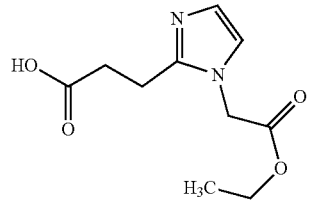 [SMILES: CCOC(=O)Cn1ccnc1CCC(=O)O]

Palladium-carbon (10% wet, 1.46 g, 1.37 mmol) was added to a solution of (E)-benzyl 3-(1-(2-ethoxy-2-oxoethyl)-1H-imidazol-2-yl)acrylate (4.31 g, 13.7 mmol) in ethanol (80.0 mL) at room temperature. The reaction liquid was stirred under a hydrogen atmosphere at the same temperature for 24 hours. The temperature of the reaction liquid was raised to 40° C. and the reaction liquid was stirred for 1 hour. The reaction liquid was filtered through Celite and the filtrate was concentrated under reduced pressure to obtain a crude product of 3-(1-(2-ethoxy-2-oxoethyl)-1H-imidazol-2-yl)propanoic acid.

Reference Example 10: Synthesis of ethyl 2-(2-(3-(4-morpholinopiperidin-1-yl)-3-oxopropyl)-1H-imidazol-1-yl)acetate

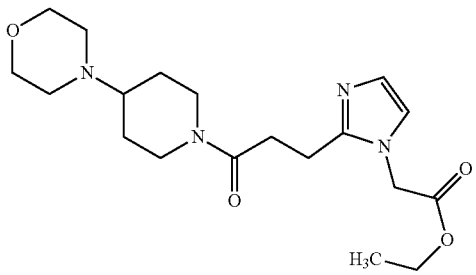 [SMILES: CCOC(=O)Cn1ccnc1CCC(=O)N1CCC(N2CCOCC2)CC1]

Diisopropylethylamine (0.171 g, 1.33 mmol), HBTU (0.402 g, 1.06 mmol) and 4-(piperidin-4-yl)morpholine (0.151 g, 0.884 mmol) were added to a solution of crude 3-(1-(2-ethoxy-2-oxoethyl)-1H-imidazol-2-yl)propanoic acid (0.200 g, 0.884 mmol) in dichloromethane (10.0 mL) at room temperature. The reaction liquid was stirred at the same temperature for 12 hours. The reaction liquid was concentrated under reduced pressure. The residue was purified by flash column chromatography (NH silica gel, n-hexane/ethyl acetate and chloroform/methanol) to obtain ethyl 2-(2-(3-(4-morpholinopiperidin-1-yl)-3-oxopropyl)-1H-imidazol-1-yl)acetate (0.265 g, 0.700 mmol, 79%) as a white solid.

$^1$H-NMR (400 MHz, CDCl$_3$) δ: 1.29 (3H, t, J=7.2 Hz), 1.30-1.45 (2H, m), 1.81-1.92 (2H, m), 2.39 (1H, tt, J=10.8, 3.6 Hz), 2.53 (4H, t, J=4.8 Hz), 2.59 (1H, td, J=13.2, 2.8 Hz), 2.91 (4H, s), 3.01 (1H, td, J=13.2, 2.8 Hz), 3.71 (4H, t, J=4.8 Hz), 3.97-4.04 (1H, m), 4.23 (2H, q, J=7.2 Hz), 4.54-4.62 (1H, m), 4.75 (2H, s), 6.82 (1H, d, J=1.6 Hz), 6.96 (1H, d, J=1.6 Hz).

ESI-MS: m/z=379 (M+H)$^+$.

Reference Example 11: Synthesis of 2-(2-(3-(4-morpholinopiperidin-1-yl)-3-oxopropyl)-1H-imidazol-1-yl)acetic acid

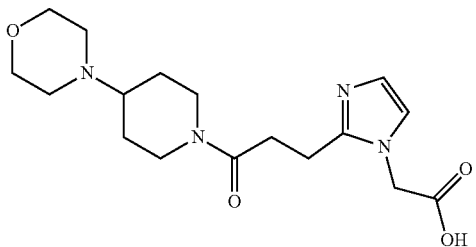 [SMILES: O=C(O)Cn1ccnc1CCC(=O)N1CCC(N2CCOCC2)CC1]

An aqueous solution of sodium hydroxide (1.0 N, 1.45 mL, 1.45 mmol) was added to a solution of ethyl 2-(2-(3-(4-morpholinopiperidin-1-yl)-3-oxopropyl)-1H-imidazol-1-yl)acetate (0.500 g, 1.32 mmol) in ethanol (1.4 mL) at room temperature. The reaction liquid was stirred at the same temperature for 2 hours. After the reaction liquid was cooled to 0° C., hydrochloric acid (1.0 N) was added to the reaction liquid to neutralize it. The reaction liquid was concentrated under reduced pressure and subjected to azeotropic distillation with toluene, and ethanol was added to the reaction liquid. The resulting precipitate was filtered through Celite and the filtrate was concentrated under reduced pressure to obtain 2-(2-(3-(4-morpholinopiperidin-1-yl)-3-oxopropyl)-1H-imidazol-1-yl)acetic acid (0.380 g, 1.08 mmol, 82%) as a white solid.

$^1$H-NMR (400 MHz, CD$_3$OD) δ: 1.44-1.76 (2H, m), 2.07-2.18 (2H, m), 2.57-2.70 (1H, m), 2.82-3.00 (2H, m), 3.05-3.35 (8H, m), 3.84-4.07 (5H, m), 4.59-4.68 (1H, m), 4.76-4.90 (2H, m), 7.35-7.43 (2H, m).

ESI-MS: 351 (M+H)$^+$.

Example 1: Synthesis of n-butyl (S)-3-(2-(3-(3-(dimethylamino)pyrrolidin-1-yl)-3-oxopropyl)-1H-imidazol-1-yl)propanoate

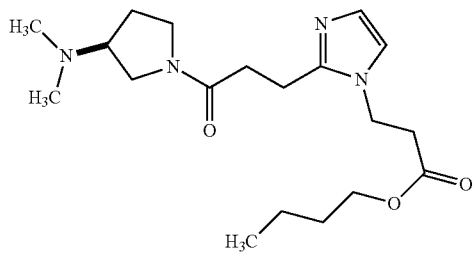 [SMILES: CCCCOC(=O)CCn1ccnc1CCC(=O)N1CC[C@H](N(C)C)C1]

Diisopropylethylamine (0.113 mL, 0.649 mmol), HBTU (0.184 g, 0.486 mmol) and butan-1-ol (0.0590 mL, 0.649 mmol) were added to a solution of (S)-3-(2-(3-(3-(dimethylamino)pyrrolidin-1-yl)-3-oxopropyl)-1H-imidazol-1-yl)propanoic acid (0.100 g, 0.324 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-butyl (S)-3-(2-(3-(3-(dimethylamino)pyrrolidin-1-yl)-3-oxopropyl)-1H-imidazol-1-yl)propanoate (0.115 g, 0.316 mmol, 97%) (hereinafter referred to as the compound of Example 1) as a colorless oil.

$^1$H-NMR (400 MHz, CDCl$_3$) δ: 0.92 (3H, t, J=7.2 Hz), 1.28-1.40 (2H, m), 1.54-1.85 (1H, m), 2.05-2.28 (8H, m), 2.56-3.53 (10H, m), 3.63-3.85 (2H, m), 4.08 (2H, t, J=7.2 Hz), 4.22-4.27 (2H, m), 6.85-6.95 (2H, m).

ESI-MS: m/z=365 (M+H)$^+$.

Example 2: Synthesis of n-butyl (S)-3-(2-(3-(3-(dimethylamino)pyrrolidin-1-yl)-3-oxopropyl)-1H-imidazol-1-yl)propanoate hydrochloride

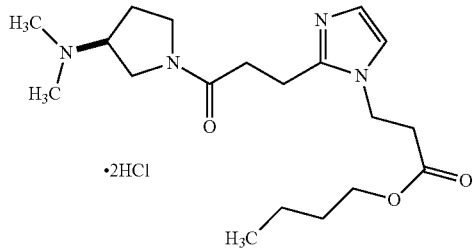 [SMILES: CCCCOC(=O)CCn1ccnc1CCC(=O)N1CC[C@H](N(C)C)C1 ; "·2HCl"]

A solution of hydrogen chloride in diethyl ether (2.0 N, 0.347 mL, 0.694 mmol) was added to a solution of n-butyl (S)-3-(2-(3-(3-(dimethylamino)pyrrolidin-1-yl)-3-oxopropyl)-1H-imidazol-1-yl)propanoate (0.115 g, 0.316 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-butyl (S)-3-(2-(3-(3-(dimethylamino)pyrrolidin-1-yl)-3-oxopropyl)-1H-imidazol-1-yl)propanoate hydrochloride (0.124 g, 0.283 mmol, 90%) (hereinafter referred to as the compound of Example 2) as a white solid.

$^1$H-NMR (400 MHz, D$_2$O) δ: 0.86 (3H, t, J=7.6 Hz), 1.22-1.36 (2H, m), 1.53-1.62 (2H, m), 2.07-2.35 (1H, m), 2.45-2.63 (1H, m), 2.99-3.07 (10H, m), 3.25-4.14 (9H, m), 4.45-4.52 (2H, m), 7.34-7.37 (1H, m), 7.41-7.44 (1H, m).

ESI-MS: as n-butyl (S)-3-(2-(3-(3-(dimethylamino)pyrrolidin-1-yl)-3-oxopropyl)-1H-imidazol-1-yl)propanoate: m/z=365 (M+H)$^+$.

Example 3: Synthesis of n-hexyl (S)-3-(2-(3-(3-(dimethylamino)pyrrolidin-1-yl)-3-oxopropyl)-1H-imidazol-1-yl)propanoate

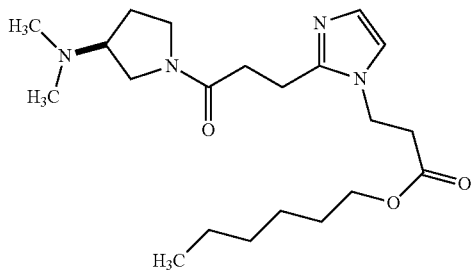 [SMILES: CCCCCCOC(=O)CCn1ccnc1CCC(=O)N1CC[C@H](N(C)C)C1]

Diisopropylethylamine (0.113 mL, 0.649 mmol), HBTU (0.184 g, 0.486 mmol) and hexane-1-ol (0.0810 mL, 0.649 mmol) were added to a solution of (S)-3-(2-(3-(3-(dimethylamino)pyrrolidin-1-yl)-3-oxopropyl)-1H-imidazol-1-yl)propanoic acid (0.100 g, 0.324 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-hexyl (S)-3-(2-(3-(3-(dimethylamino)pyrrolidin-1-yl)-3-oxopropyl)-1H-imidazol-1-yl)propanoate (0.0700 g, 0.178 mmol, 55%) (hereinafter referred to as the compound of Example 3) as a colorless oil.

$^1$H-NMR (400 MHz, CDCl$_3$) δ: 0.82-0.92 (3H, m), 1.22-1.38 (8H, m), 1.65-1.92 (1H, m), 2.05-2.27 (7H, m), 2.55-3.52 (9H, m), 3.62-3.85 (2H, m), 4.07 (2H, t, J=7.2 Hz), 4.22-4.28 (2H, m), 6.83-6.86 (1H, m), 6.89-6.92 (1H, m).

ESI-MS: m/z=393 (M+H)$^+$.

Example 4: Synthesis of n-hexyl (S)-3-(2-(3-(3-(dimethylamino)pyrrolidin-1-yl)-3-oxopropyl)-1H-imidazol-1-yl)propanoate hydrochloride

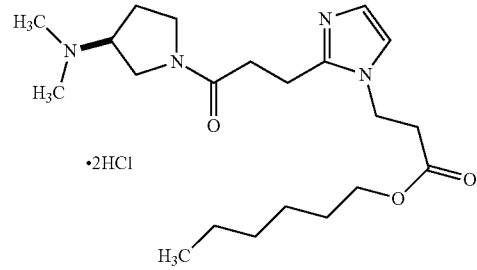 [SMILES: CCCCCCOC(=O)CCn1ccnc1CCC(=O)N1CC[C@H](N(C)C)C1 ; "·2HCl"]

A solution of hydrogen chloride in diethyl ether (2.0 N, 0.196 mL, 0.392 mmol) was added to a solution of n-hexyl (S)-3-(2-(3-(3-(dimethylamino)pyrrolidin-1-yl)-3-oxopropyl)-1H-imidazol-1-yl)propanoate (0.0700 g, 0.178 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-hexyl (S)-3-(2-(3-(3-(dimethylamino)pyrrolidin-1-yl)-3-oxopropyl)-1H-imidazol-1-yl)propanoate hydrochloride (0.0649 g, 0.139 mmol, 78%) (hereinafter referred to as the compound of Example 4) as a white solid.

$^1$H-NMR (400 MHz, D$_2$O) δ: 0.80-0.88 (3H, m), 1.20-1.40 (6H, m), 1.53-1.63 (2H, m), 2.05-2.32 (1H, m), 2.42-2.61 (1H, m), 2.89-3.04 (10H, m), 3.20-3.27 (2H, m), 3.38-4.15 (7H, m), 4.44 (2H, t, J=6.4 Hz), 7.23-7.38 (2H, m).

ESI-MS: as n-hexyl (S)-3-(2-(3-(3-(dimethylamino)pyrrolidin-1-yl)-3-oxopropyl)-1H-imidazol-1-yl)propanoate: m/z=393 (M+H)$^+$.

Example 5: Synthesis of n-heptyl (S)-3-(2-(3-(3-(dimethylamino)pyrrolidin-1-yl)-3-oxopropyl)-1H-imidazol-1-yl)propanote

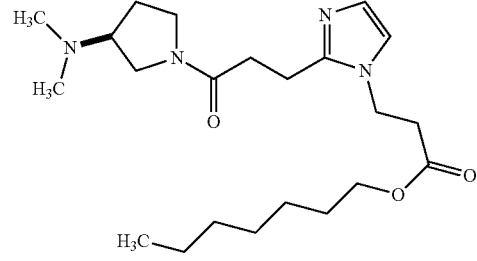 [SMILES: CCCCCCCOC(=O)CCn1ccnc1CCC(=O)N1CC[C@H](N(C)C)C1]

Diisopropylethylamine (0.113 mL, 0.649 mmol), HBTU (0.184 g, 0.486 mmol) and heptan-1-ol (0.0920 mL, 0.649 mmol) were added to a solution of (S)-3-(2-(3-(3-(dimethylamino)pyrrolidin-1-yl)-3-oxopropyl)-1H-imidazol-1-yl)propanoic acid (0.100 g, 0.324 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-heptyl (S)-3-(2-(3-(3-(dimethylamino)pyrrolidin-1-yl)-3-oxopropyl)-1H-imidazol-1-yl)propanote (0.0950 g, 0.234 mmol, 72%) (hereinafter referred to as the compound of Example 5) as a colorless oil.

$^1$H-NMR (400 MHz, CDCl$_3$) δ: 0.85-0.92 (3H, m), 1.22-1.34 (8H, m), 1.58-1.90 (4H, m), 2.04-2.27 (7H, m), 2.56-3.52 (8H, m), 3.63-3.85 (2H, m), 4.07 (2H, t, J=6.8 Hz), 4.22-4.28 (2H, m), 6.84-6.86 (1H, m), 6.90-6.92 (1H, m).

ESI-MS: m/z=407 (M+H)$^+$.

Example 6: Synthesis of n-heptyl (S)-3-(2-(3-(3-(dimethylamino)pyrrolidin-1-yl)-3-oxopropyl)-1H-imidazol-1-yl)propanote hydrochloride

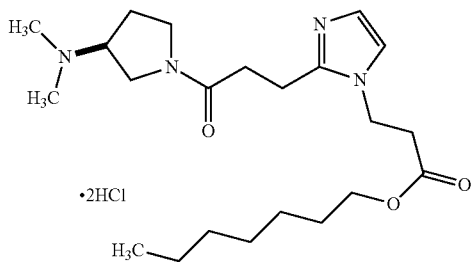 [SMILES: CCCCCCCOC(=O)CCn1ccnc1CCC(=O)N1CC[C@H](N(C)C)C1]

A solution of hydrogen chloride in diethyl ether (2.0 N, 0.257 mL, 0.514 mmol) was added to a solution of n-heptyl (S)-3-(2-(3-(3-(dimethylamino)pyrrolidin-1-yl)-3-oxopropyl)-1H-imidazol-1-yl)propanote (0.0950 g, 0.234 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-heptyl (S)-3-(2-(3-(3-(dimethylamino)pyrrolidin-1-yl)-3-oxopropyl)-1H-imidazol-1-yl)propanote hydrochloride (0.0740 g, 0.154 mmol, 66%) (hereinafter referred to as the compound of Example 6) as a white solid.

$^1$H-NMR (400 MHz, D$_2$O) δ: 0.82-0.90 (3H, m), 1.18-1.30 (8H, m), 1.54-1.65 (2H, m), 2.05-2.35 (1H, m), 2.45-2.64 (1H, m), 2.92-2.98 (8H, m), 3.01-3.08 (2H, m), 3.26-3.34 (2H, m), 3.39-4.16 (7H, m), 4.45-4.52 (2H, m), 7.30-7.45 (2H, m).

ESI-MS: as n-heptyl (S)-3-(2-(3-(3-(dimethylamino)pyrrolidin-1-yl)-3-oxopropyl)-1H-imidazol-1-yl)propanoate: m/z=407 (M+H)$^+$.

Example 7: Synthesis of n-octyl (S)-3-(2-(3-(3-(dimethylamino)pyrrolidin-1-yl)-3-oxopropyl)-1H-imidazol-1-yl)propanoate

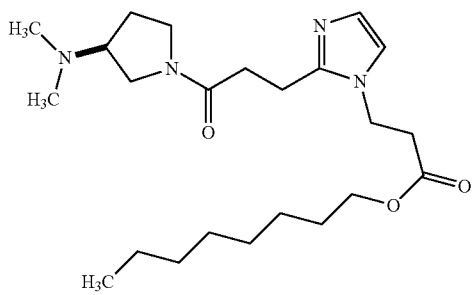 [SMILES: CCCCCCCCOC(=O)CCn1ccnc1CCC(=O)N1CC[C@H](N(C)C)C1]

Diisopropylethylamine (0.113 mL, 0.649 mmol), HBTU (0.184 g, 0.486 mmol) and octan-1-ol (0.103 mL, 0.649 mmol) were added to a solution of (S)-3-(2-(3-(3-(dimethylamino)pyrrolidin-1-yl)-3-oxopropyl)-1H-imidazol-1-yl)propanoic acid (0.100 g, 0.324 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-octyl (S)-3-(2-(3-(3-(dimethylamino)pyrrolidin-1-yl)-3-oxopropyl)-1H-imidazol-1-yl)propanoate (0.0850 g, 0.202 mmol, 62%) (hereinafter referred to as the compound of Example 7) as a colorless oil.

$^1$H-NMR (400 MHz, CDCl$_3$) δ: 0.84-0.92 (3H, m), 1.20-1.36 (10H, m), 1.55-1.90 (2H, m), 2.02-2.18 (2H, m), 2.26 (6H, s), 2.57-3.85 (11H, m), 4.07 (2H, t, J=6.8 Hz), 4.20-4.27 (2H, m), 6.82-6.92 (2H, m).

ESI-MS: m/z=421 (M+H)$^+$.

Example 8: Synthesis of n-octyl (S)-3-(2-(3-(3-(dimethylamino)pyrrolidin-1-yl)-3-oxopropyl)-1H-imidazol-1-yl)propanoate hydrochloride

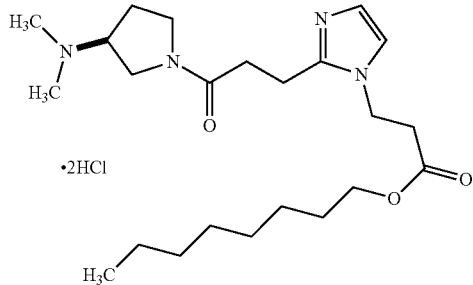 [SMILES: CCCCCCCCOC(=O)CCn1ccnc1CCC(=O)N1CC[C@H](N(C)C)C1]

A solution of hydrogen chloride in diethyl ether (2.0 N, 0.222 mL, 0.444 mmol) was added to a solution of n-octyl (S)-3-(2-(3-(3-(dimethylamino)pyrrolidin-1-yl)-3-oxopropyl)-1H-imidazol-1-yl)propanoate (0.0850 g, 0.202 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-octyl (S)-3-(2-(3-(3-(dimethylamino)pyrrolidin-1-yl)-3-oxopropyl)-1H-imidazol-1-yl)propanoate hydrochloride (0.0733 g, 0.149 mmol, 74%) (hereinafter referred to as the compound of Example 8) as a white solid.

$^1$H-NMR (400 MHz, D$_2$O) δ: 0.84 (3H, t, J=6.8 Hz), 1.18-1.35 (10H, m), 1.52-1.62 (2H, m), 2.04-2.30 (1H, m), 2.40-2.60 (1H, m), 2.84-2.94 (8H, m), 2.97-3.04 (2H, m), 3.17-3.27 (2H, m), 3.36-4.14 (7H, m), 4.39-4.46 (2H, m), 7.20-7.38 (2H, m).

ESI-MS: as n-octyl (S)-3-(2-(3-(3-(dimethylamino)pyrrolidin-1-yl)-3-oxopropyl)-1H-imidazol-1-yl)propanoate: m/z=421 (M+H)$^+$.

Example 9: Synthesis of n-propyl 2-(2-(3-(4-morpholinopiperidin-1-yl)-3-oxopropyl)-1H-imidazol-1-yl)acetate

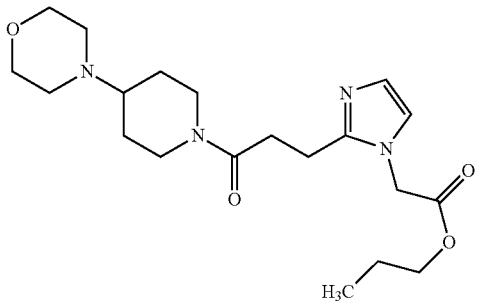 [SMILES: CCCOC(=O)Cn1ccnc1CCC(=O)N1CCC(N2CCOCC2)CC1]

Diisopropylethylamine (0.199 mL, 1.14 mmol), HBTU (0.325 g, 0.856 mmol) and propan-1-ol (0.0860 mL, 1.14 mmol) were added to a solution of 2-(2-(3-(4-morpholinopiperidin-1-yl)-3-oxopropyl)-1H-imidazol-1-yl)acetic acid (0.200 g, 0.571 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-propyl 2-(2-(3-(4-morpholinopiperidin-1-yl)-3-oxopropyl)-1H-imidazol-1-yl)acetate (0.201 g, 0.512 mmol, 90%) (hereinafter referred to as the compound of Example 9) as a colorless oil.

$^1$H-NMR (400 MHz, CDCl$_3$) δ: 0.90-0.98 (3H, m), 1.29-1.48 (2H, m), 1.54-1.72 (4H, m), 2.34-2.65 (6H, m), 2.88-3.05 (5H, m), 3.68-3.76 (4H, m), 3.95-4.05 (1H, m), 4.10-4.14 (2H, m), 4.54-4.64 (1H, m), 4.76 (2H, s), 6.81-6.83 (1H, m), 6.96-6.98 (1H, m).

ESI-MS: m/z=393 (M+H)$^+$.

Example 10: Synthesis of n-propyl 2-(2-(3-(4-morpholinopiperidin-1-yl)-3-oxopropyl)-1H-imidazol-1-yl)acetate hydrochloride

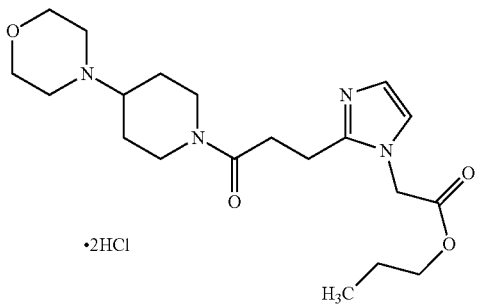 [SMILES: CCCOC(=O)Cn1ccnc1CCC(=O)N1CCC(N2CCOCC2)CC1]

A solution of hydrogen chloride in diethyl ether (2.0 N, 0.560 mL, 1.12 mmol) was added to a solution of n-propyl 2-(2-(3-(4-morpholinopiperidin-1-yl)-3-oxopropyl)-1H-imidazol-1-yl)acetate (0.201 g, 0.512 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-propyl 2-(2-(3-(4-morpholinopiperidin-1-yl)-3-oxopropyl)-1H-imidazol-1-yl)acetate hydrochloride (0.160 g, 0.344 mmol, 67%) (hereinafter referred to as the compound of Example 10) as a white solid.

$^1$H-NMR (400 MHz, D$_2$O) δ: 0.85-0.95 (3H, m), 1.48-1.73 (4H, m), 2.17-2.27 (2H, m), 2.65-2.75 (1H, m), 2.96-3.04 (2H, m), 3.10-4.12 (13H, m), 4.18-4.24 (2H, m), 4.47-4.57 (1H, m), 5.17 (2H, s), 7.35-7.37 (2H, m).

ESI-MS: as n-propyl 2-(2-(3-(4-morpholinopiperidin-1-yl)-3-oxopropyl)-1H-imidazol-1-yl)acetate: m/z=393 (M+H)$^+$.

Example 11: Synthesis of n-butyl 2-(2-(3-(4-morpholinopiperidin-1-yl)-3-oxopropyl)-1H-imidazol-1-yl)acetate

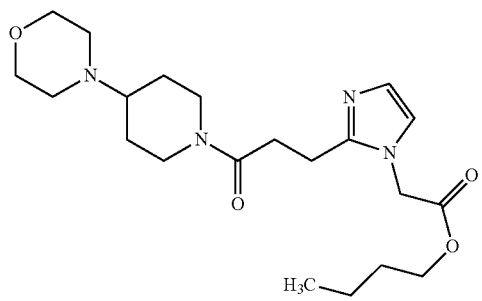 [SMILES: CCCCOC(=O)Cn1ccnc1CCC(=O)N1CCC(N2CCOCC2)CC1]

Diisopropylethylamine (0.100 mL, 0.571 mmol), HBTU (0.162 g, 0.428 mmol) and butan-1-ol (0.0520 mL, 0.571 mmol) were added to a solution of 2-(2-(3-(4-morpholinopiperidin-1-yl)-3-oxopropyl)-1H-imidazol-1-yl)acetic acid (0.100 g, 0.285 mmol) in chloroform (3.0 mL) at room temperature and the reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-butyl 2-(2-(3-(4-morpholinopiperidin-1-yl)-3-oxopropyl)-1H-imidazol-1-yl)acetate (0.0980 g, 0.241 mmol, 85%) (hereinafter referred to as the compound of Example 11) as a colorless oil.

$^1$H-NMR (400 MHz, CDCl$_3$) δ: 0.93 (3H, t, J=7.6 Hz), 1.23-1.66 (6H, m), 1.80-1.90 (2H, m), 2.34-2.44 (1H, m), 2.50-2.64 (5H, m), 2.89-3.05 (5H, m), 3.68-3.74 (4H, m), 3.96-4.04 (1H, m), 4.08-4.19 (2H, m), 4.53-4.61 (1H, m), 4.75 (2H, s), 6.80-6.82 (1H, m), 6.91-6.93 (1H, m).

ESI-MS: m/z=407 (M+H)$^+$.

Example 12: Synthesis of n-butyl 2-(2-(3-(4-morpholinopiperidin-1-yl)-3-oxopropyl)-1H-imidazol-1-yl)acetate hydrochloride

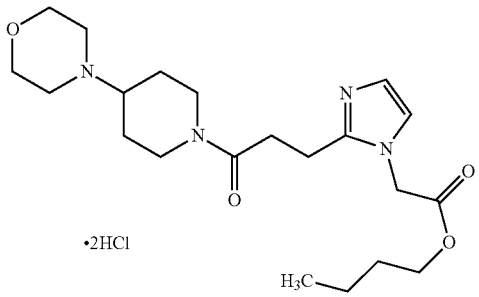 [SMILES: CCCCOC(=O)Cn1ccnc1CCC(=O)N1CCC(N2CCOCC2)CC1]

A solution of hydrogen chloride in diethyl ether (2.0 N, 0.265 mL, 0.530 mmol) was added to a solution of n-butyl 2-(2-(3-(4-morpholinopiperidin-1-yl)-3-oxopropyl)-1H-imidazol-1-yl)acetate (0.0980 g, 0.241 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-butyl 2-(2-(3-(4-morpholinopiperidin-1-yl)-3-oxopropyl)-1H-imidazol-1-yl)acetate hydrochloride (0.0790 g, 0.165 mmol, 68%) (hereinafter referred to as the compound of Example 12) as a white solid.

$^1$H-NMR (400 MHz, D$_2$O) δ: 0.85-0.93 (3H, m), 1.28-1.40 (2H, m), 1.50-1.76 (4H, m), 2.19-2.29 (2H, m), 2.67-2.77 (1H, m), 2.98-3.04 (2H, m), 3.12-3.60 (8H, m), 3.75-4.20 (5H, m), 4.23-4.30 (2H, m), 4.48-4.58 (1H, m), 5.19 (2H, m), 7.38-7.43 (2H, m).

ESI-MS: as n-butyl 2-(2-(3-(4-morpholinopiperidin-1-yl)-3-oxopropyl)-1H-imidazol-1-yl)acetate: m/z=407 (M+H)$^+$.

Example 13: Synthesis of n-pentyl 2-(2-(3-(4-morpholinopiperidin-1-yl)-3-oxopropyl)-1H-imidazol-1-yl)acetate

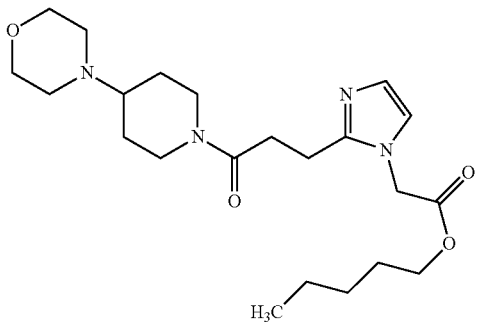 [SMILES: CCCCCOC(=O)Cn1ccnc1CCC(=O)N1CCC(N2CCOCC2)CC1]

Diisopropylethylamine (0.199 mL, 1.14 mmol), HBTU (0.325 g, 0.856 mmol) and pentan-1-ol (0.124 mL, 1.14 mmol) were added to a solution of 2-(2-(3-(4-morpholinopiperidin-1-yl)-3-oxopropyl)-1H-imidazol-1-yl)acetic acid (0.200 g, 0.571 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-pentyl 2-(2-(3-(4-morpholinopiperidin-1-yl)-3-oxopropyl)-1H-imidazol-1-yl)acetate (0.199 g, 0.473 mmol, 83%) (hereinafter referred to as the compound of Example 13) as a colorless oil.

$^1$H-NMR (400 MHz, CDCl$_3$) δ: 0.85-0.94 (3H, m), 1.22-1.45 (6H, m), 1.55-1.68 (2H, m), 1.80-1.90 (2H, m), 2.34-2.44 (1H, m), 2.48-2.65 (5H, m), 2.88-3.05 (5H, m), 3.67-3.74 (4H, m), 3.95-4.05 (1H, m), 4.13-4.18 (2H, m), 4.52-4.62 (1H, m), 4.75 (2H, s), 6.80-6.83 (1H, m), 6.95-6.98 (1H, m).

ESI-MS: m/z=421 (M+H)$^+$.

Example 14: Synthesis of n-pentyl 2-(2-(3-(4-morpholinopiperidin-1-yl)-3-oxopropyl)-1H-imidazol-1-yl)acetate hydrochloride

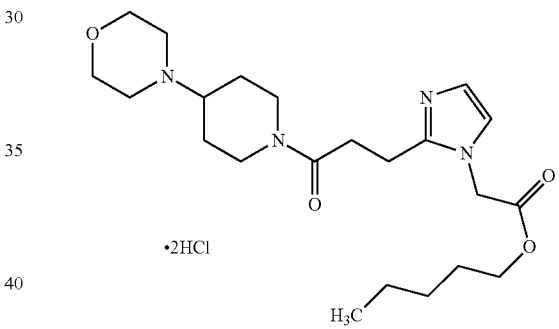

A solution of hydrogen chloride in diethyl ether (2.0 N, 0.521 mL, 1.04 mmol) was added to a solution of n-pentyl 2-(2-(3-(4-morpholinopiperidin-1-yl)-3-oxopropyl)-1H-imidazol-1-yl)acetate (0.199 g, 0.473 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-pentyl 2-(2-(3-(4-morpholinopiperidin-1-yl)-3-oxopropyl)-1H-imidazol-1-yl)acetate hydrochloride (0.181 g, 0.367 mmol, 78%) (hereinafter referred to as the compound of Example 14) as a white solid.

$^1$H-NMR (400 MHz, D$_2$O) δ: 0.83-0.88 (3H, m), 1.25-1.33 (4H, m), 1.45-1.72 (4H, m), 2.15-2.25 (2H, m), 2.65-2.75 (1H, m), 2.95-3.02 (2H, m), 3.12-4.13 (13H, m), 4.20-4.26 (2H, m), 4.48-4.56 (1H, m), 5.15 (2H, s), 7.30-7.35 (2H, m).

ESI-MS: as n-pentyl 2-(2-(3-(4-morpholinopiperidin-1-yl)-3-oxopropyl)-1H-imidazol-1-yl)acetate: m/z=421 (M+H)$^+$.

Example 15: Synthesis of n-hexyl 2-(2-(3-(4-morpholinopiperidin-1-yl)-3-oxopropyl)-1H-imidazol-1-yl)acetate

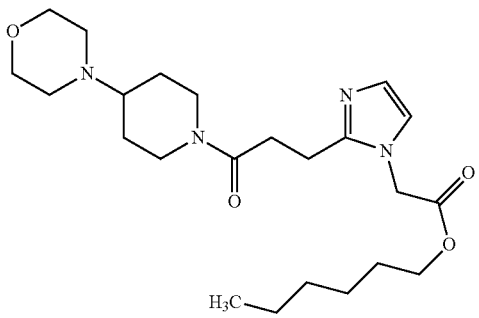 [SMILES: CCCCCCOC(=O)Cn1ccnc1CCC(=O)N1CCC(N2CCOCC2)CC1]

Diisopropylethylamine (0.100 mL, 0.571 mmol), HBTU (0.162 g, 0.428 mmol) and hexane-1-ol (0.0370 mL, 0.405 mmol) were added to a solution of 2-(2-(3-(4-morpholinopiperidin-1-yl)-3-oxopropyl)-1H-imidazol-1-yl)acetic acid (0.100 g, 0.285 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-hexyl 2-(2-(3-(4-morpholinopiperidin-1-yl)-3-oxopropyl)-1H-imidazol-1-yl)acetate (0.0950 g, 0.219 mmol, 77%) (hereinafter referred to as the compound of Example 15) as a colorless oil.

$^1$H-NMR (400 MHz, CDCl$_3$) δ: 0.85-0.93 (3H, m), 1.24-1.45 (8H, m), 1.58-1.64 (2H, m), 1.80-1.91 (2H, m), 2.38-2.44 (1H, m), 2.50-2.64 (5H, m), 2.89-3.05 (5H, m), 3.68-3.74 (4H, m), 3.95-4.04 (1H, m), 4.12-4.18 (2H, m), 4.53-4.60 (1H, m), 4.75 (2H, s), 6.80-6.82 (1H, m), 6.95-6.97 (1H, m).

ESI-MS: m/z=435 (M+H)$^+$.

Example 16: Synthesis of n-hexyl 2-(2-(3-(4-morpholinopiperidin-1-yl)-3-oxopropyl)-1H-imidazol-1-yl)acetate hydrochloride

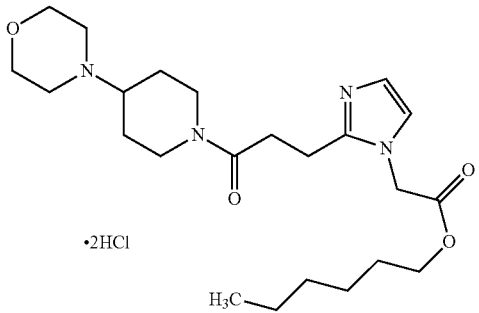 [SMILES: CCCCCCOC(=O)Cn1ccnc1CCC(=O)N1CCC(N2CCOCC2)CC1]

A solution of hydrogen chloride in diethyl ether (2.0 N, 0.240 mL, 0.480 mmol) was added to a solution of n-hexyl 2-(2-(3-(4-morpholinopiperidin-1-yl)-3-oxopropyl)-1H-imidazol-1-yl)acetate (0.0950 g, 0.219 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-hexyl 2-(2-(3-(4-morpholinopiperidin-1-yl)-3-oxopropyl)-1H-imidazol-1-yl)acetate hydrochloride (0.0809 g, 0.159 mmol, 73%) (hereinafter referred to as the compound of Example 16) as a white solid.

$^1$H-NMR (400 MHz, D$_2$O) δ: 0.84 (3H, t, J=6.4 Hz), 1.23-1.35 (6H, m), 1.50-1.75 (4H, m), 2.18-2.30 (2H, m), 2.67-2.76 (1H, m), 2.98-3.05 (2H, m), 3.13-3.63 (8H, m), 3.74-4.28 (7H, m), 4.48-4.57 (1H, m), 5.17-5.22 (2H, m), 7.37-7.42 (2H, m).

ESI-MS: as n-hexyl 2-(2-(3-(4-morpholinopiperidin-1-yl)-3-oxopropyl)-1H-imidazol-1-yl)acetate: m/z=435 (M+H)$^+$.

Example 17: Synthesis of n-heptyl 2-(2-(3-(4-morpholinopiperidin-1-yl)-3-oxopropyl)-1H-imidazol-1-yl)acetate

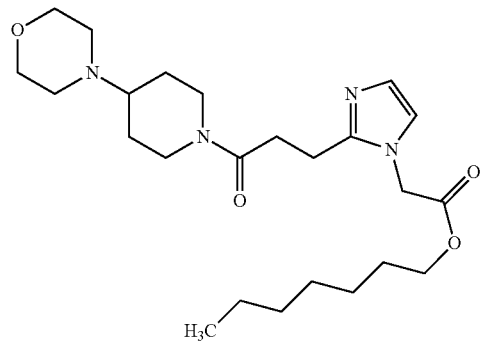 [SMILES: CCCCCCCOC(=O)Cn1ccnc1CCC(=O)N1CCC(N2CCOCC2)CC1]

Diisopropylethylamine (0.100 mL, 0.571 mmol), HBTU (0.162 g, 0.428 mmol) and heptan-1-ol (0.0810 mL, 0.571 mmol) were added to a solution of 2-(2-(3-(4-morpholinopiperidin-1-yl)-3-oxopropyl)-1H-imidazol-1-yl)acetic acid (0.100 g, 0.285 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-heptyl 2-(2-(3-(4-morpholinopiperidin-1-yl)-3-oxopropyl)-1H-imidazol-1-yl)acetate (0.110 g, 0.245 mmol, 86%) (hereinafter referred to as the compound of Example 17) as a colorless oil.

$^1$H-NMR (400 MHz, CDCl$_3$) δ: 0.86-0.92 (3H, m), 1.20-1.46 (10H, m), 1.55-1.65 (2H, m), 1.80-1.91 (2H, m), 2.34-2.44 (1H, m), 2.48-2.64 (5H, m), 2.89-2.92 (4H, m), 2.96-3.04 (1H, m), 3.68-3.73 (4H, m), 3.96-4.04 (1H, m), 4.15 (2H, t, J=6.8 Hz), 4.53-4.61 (1H, m), 4.75 (2H, s), 6.80-6.82 (1H, m), 6.95-6.97 (1H, m).

ESI-MS: m/z=449 (M+H)$^+$.

Example 18: Synthesis of n-heptyl 2-(2-(3-(4-morpholinopiperidin-1-yl)-3-oxopropyl)-1H-imidazol-1-yl)acetate hydrochloride

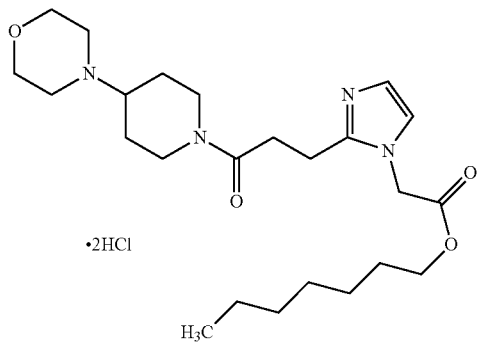 [SMILES: CCCCCCCOC(=O)Cn1ccnc1CCC(=O)N1CCC(N2CCOCC2)CC1]

A solution of hydrogen chloride in diethyl ether (2.0 N, 0.270 mL, 0.540 mmol) was added to a solution of n-heptyl 2-(2-(3-(4-morpholinopiperidin-1-yl)-3-oxopropyl)-1H-imidazol-1-yl)acetate (0.110 g, 0.245 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-heptyl 2-(2-(3-(4-morpholinopiperidin-1-yl)-3-oxopropyl)-1H-imidazol-1-yl)acetate hydrochloride (0.0819 g, 0.157 mmol, 64%) (hereinafter referred to as the compound of Example 18) as a white solid.

$^1$H-NMR (400 MHz, D$_2$O) δ: 0.82-0.88 (3H, m), 1.20-1.34 (8H, m), 1.46-1.70 (4H, m), 2.15-2.26 (2H, m), 2.65-2.75 (1H, m), 2.94-3.02 (2H, m), 3.10-4.12 (13H, m), 4.24 (2H, t, J=6.4 Hz), 4.47-4.66 (1H, m), 5.12 (2H, s), 7.26-7.34 (2H, m).

ESI-MS: as n-heptyl 2-(2-(3-(4-morpholinopiperidin-1-yl)-3-oxopropyl)-1H-imidazol-1-yl)acetate: m/z=449 (M+H)$^+$.

Example 19: Synthesis of n-octyl 2-(2-(3-(4-morpholinopiperidin-1-yl)-3-oxopropyl)-1H-imidazol-1-yl)acetate

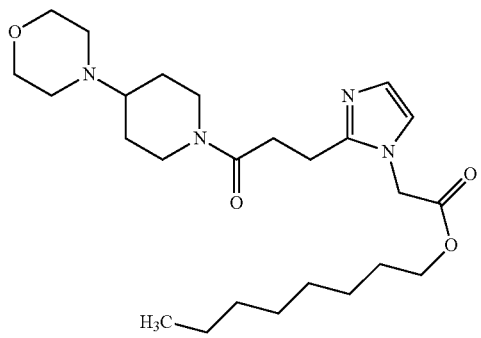 [SMILES: CCCCCCCCOC(=O)Cn1ccnc1CCC(=O)N1CCC(N2CCOCC2)CC1]

Diisopropylethylamine (0.100 mL, 0.571 mmol), HBTU (0.162 g, 0.428 mmol) and octan-1-ol (0.0900 mL, 0.571 mmol) were added to a solution of 2-(2-(3-(4-morpholinopiperidin-1-yl)-3-oxopropyl)-1H-imidazol-1-yl)acetic acid (0.100 g, 0.285 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by flash column chromatography (NH silica gel, chloroform/methanol) to obtain n-octyl 2-(2-(3-(4-morpholinopiperidin-1-yl)-3-oxopropyl)-1H-imidazol-1-yl)acetate (0.0980 g, 0.212 mmol, 74%) (hereinafter referred to as the compound of Example 19) as a colorless oil.

$^1$H-NMR (400 MHz, CDCl$_3$) δ: 0.84-0.92 (3H, m), 1.20-1.45 (12H, m), 1.55-1.65 (2H, m), 1.80-1.92 (2H, m), 2.32-2.44 (1H, m), 2.49-2.64 (5H, m), 2.87-3.05 (5H, m), 3.66-3.74 (4H, m), 3.94-4.05 (1H, m), 4.15 (2H, t, J=6.8 Hz), 4.53-4.63 (1H, m), 4.75 (2H, s), 6.80-6.84 (1H, m), 6.94-6.98 (1H, m).

ESI-MS: m/z=463 (M+H)$^+$.

Example 20: Synthesis of n-octyl 2-(2-(3-(4-morpholinopiperidin-1-yl)-3-oxopropyl)-1H-imidazol-1-yl)acetate hydrochloride

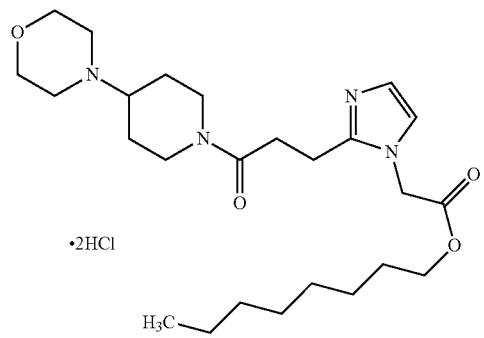 [SMILES: CCCCCCCCOC(=O)Cn1ccnc1CCC(=O)N1CCC(N2CCOCC2)CC1]

A solution of hydrogen chloride in diethyl ether (2.0 N, 0.233 mL, 0.466 mmol) was added to a solution of n-octyl 2-(2-(3-(4-morpholinopiperidin-1-yl)-3-oxopropyl)-1H-imidazol-1-yl)acetate (0.0980 g, 0.212 mmol) in diethyl ether (2.0 mL) at 0° C. The reaction liquid was stirred at the same temperature for 30 minutes. The white solid precipitated was filtered and collected, washed with diethyl ether (8.0 mL) and dried at room temperature for 36 hours to obtain n-octyl 2-(2-(3-(4-morpholinopiperidin-1-yl)-3-oxopropyl)-1H-imidazol-1-yl)acetate hydrochloride (0.755 g, 0.141 mmol, 66%) (hereinafter referred to as the compound of Example 20) as a white solid.

$^1$H-NMR (400 MHz, D$_2$O) δ: 0.85 (3H, t, J=6.8 Hz), 1.20-1.35 (10H, m), 1.52-1.77 (4H, m), 2.18-2.30 (2H, m), 2.67-2.76 (1H, m), 2.97-3.05 (2H, m), 3.13-3.59 (8H, m), 3.74-4.28 (7H, m), 4.48-4.67 (1H, m), 5.20 (2H, s), 7.38-7.42 (2H, m).

ESI-MS: as n-octyl 2-(2-(3-(4-morpholinopiperidin-1-yl)-3-oxopropyl)-1H-imidazol-1-yl)acetate: m/z=463 (M+H)$^+$.

Example 21: Effect on Mouse Partial Sciatic Nerve Ligation Model

Using a partial sciatic nerve ligation model (Seltzer model) in mice by which neuropathic pain can be evaluated, the analgesic action of a cyclic amine derivative (I) or a pharmacologically acceptable salt thereof was investigated.

As the cyclic amine derivative (I) or a pharmacologically acceptable salt thereof, the compound of Example 4, 6, 8, 10, 12, 14, 16, 18 or 20 was used for evaluation.

1. Experimental Method:

The mouse partial sciatic nerve ligation model was prepared in accordance with the method of Seltzer et al. (Malmberg et al., Pain, vol. 76, p. 215-222, 1998).

Crl: CD1 (ICR) mice (5 weeks old, male; from CHARLES RIVER LABORATORIES JAPAN, INC.) was anesthetized with sodium pentobarbital (70 mg/kg, intraperitoneal administration). The sciatic nerve at the femoral region of the right hind paw of each mouse was exposed and triply ligated tightly with silk suture of 8-0 (from NATSUME SEISAKUSHO CO., LTD.) under a stereomicroscope so that only half thickness of the nerve was trapped in the ligature. A group of mice thus treated was designated as a partial sciatic nerve ligation group. A group of mice whose sciatic nerve was just exposed and not ligated was designated as a sham surgery group.

Evaluation of neuropathic pain (hereinafter referred to as von Frey test) was performed as follows. Mice were conditioned for at least one hour in an acrylic cage for measurement (from NATSUME SEISAKUSHO CO. LTD.) placed on a wire net. Thereafter, using a filament (from North Coast Medical or neuroscience) which exerted a pressure of 0.16 g, the mice were subjected to mechanical tactile stimulus by applying the filament to the plantar surface of the right hind paw 3 times, each for 3 seconds, with an interval of 3 seconds. The withdrawal response observed during each mechanical tactile stimulus was scored (0, no response; 1, showed slow and/or slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the sum of the scores obtained in the triplicate trials (hereinafter referred to as the total score) were used as a pain index.

Seven days after the sciatic nerve ligation surgery, the compound of Example 4, 6, 8, 10, 12, 14, 16, 18 or 20 (1 to 10 mg/kg for each of the compounds of Examples 4, 6 and 8, 0.1 to 10 mg/kg for each of the compounds of Examples 16 and 18, 0.01 to 10 mg/kg for each of the compounds of Examples 10, 12 and 14; and 0.1 to 1 mg/kg for the compound of Example 20) or pregabalin as a positive control (10 mg/kg; KEMPROTEC) was dissolved in distilled water and orally administered to mice of the partial sciatic nerve ligation group. The groups of the partial sciatic nerve ligation mice to which the compound of Example 4, 6, 8, 10, 12, 14, 16, 18 or 20 was administered were designated as a "partial sciatic nerve ligation+the compound of Example 4" group; a "partial sciatic nerve ligation+the compound of Example 6" group; a "partial sciatic nerve ligation+the compound of Example 8" group; a "partial sciatic nerve ligation+the compound of Example 10" group; a "partial sciatic nerve ligation+the compound of Example 12" group; a "partial sciatic nerve ligation+the compound of Example 14" group; a "partial sciatic nerve ligation+the compound of Example 16" group; a "partial sciatic nerve ligation+the compound of Example 18" group; and a "partial sciatic nerve ligation+the compound of Example 20" group, respectively. The partial sciatic nerve ligation mouse group to which pregabalin was administered, was designated as a "partial sciatic nerve ligation+pregabalin" group. Also, the partial sciatic nerve ligation mouse group to which distilled water was orally administered, was designated as a "partial sciatic nerve ligation+distilled water" group. The sham surgery mouse group to which distilled water was orally administered was designated as a "sham surgery+distilled water" group.

The von Frey test was carried out before oral administration of a test compound (pre-value), one hour, two hours and three hours after the oral administration of a test compound.

2. Results:

The results are shown in FIGS. 1 to 9. In the figures, the vertical axis represents the total score (mean value±standard error; n=5 to 6 in FIGS. 1 to 9) in the von Frey test. The higher numerical value indicates stronger pain. The horizontal axis represents time (hr) after administration of a test compound. Efficacy was statistically evaluated by a two-sample unpaired Welch's test or the Shirley-Williams test using the "partial sciatic nerve ligation+distilled water" group ("partial sciatic nerve ligation+distilled water" in the figure) of every measurement time as a control. In the figures, mark "§ or #" indicates that the value is statistically significant compared to the "partial sciatic nerve ligation+distilled water" group (§: Welch's test (p<0.05), #: the Shirley-Williams test (p<0.025)).

According to the results of the von Frey test, oral administration of the compound of Example 4, 6, 8, 10, 12, 14, 16, 18 or 20 ("partial sciatic nerve ligation+the compound of Example 4, 6, 8, 10, 12, 14, 16, 18 or 20" in the figures) showed a statistically significant analgesic action similarly to the positive control, pregabalin ("partial sciatic nerve ligation+pregabalin" in the figures).

These results clearly demonstrated that a cyclic amine derivative (I) or a pharmacologically acceptable salt thereof has a strong analgesic effect on neuropathic pain.

Example 22: Effect on Fibromyalgia Syndrome Model in Rats

Using a fibromyalgia syndrome model in rats by which fibromyalgia syndrome can be evaluated, the analgesic action of a cyclic amine derivative (I) or a pharmacologically acceptable salt thereof was investigated.

As the cyclic amine derivative (I) or a pharmacologically acceptable salt thereof, the compound of Example 6 or 18 was used for evaluation.

1. Experimental Method:

To prepare a fibromyalgia syndrome model rat (Sluka et al., Journal of Pharmacology and Experimental Therapeutics, vol. 302, p. 1146-1150, 2002; Nagakura et al., Pain, vol. 146, p. 26-33, 2009; Sluka et al., Pain, vol. 146, p. 3-4, 2009), which is generally employed widely in basic research for fibromyalgia syndrome, acidic saline (100 µL) adjusted to pH4.0 was intramuscularly injected to the gastrocnemius muscle of the right hind paw of Crl: CD(SD) rat (6 to 7 weeks old, male; from CHARLES RIVER LABORATORIES JAPAN, INC.) under continuous inhalation anesthesia with isoflurane, twice (once in each day of Day 1 and Day 6, wherein Day 1 was the date on which the acidic saline was initially administrated). The rats thus prepared were raised in a breeding room controlled at an indoor temperature of 21 to 25° C. and an indoor humidity of 40 to 70% under the conditions of voluntary intake of food and water. In the same manner, rats to which physiological saline in place of acidic saline was intramuscularly injected were raised. The rats thus raised and not afflicted with fibromyalgia syndrome ("physiological saline+distilled water" group in FIG. 10 or 11) were also used in the experiment.

Seven days after the initial administration of acidic saline, allodynia in each rat was measured. The rats, which exhibited a 50% response threshold (mean value of the right hind paw and the left hind paw) of 2 g or more to 6 g or less, were selected as fibromyalgia syndrome model rats with the onset of fibromyalgia syndrome and subjected to the following administration experiment. Measurement of allodynia was performed by use of a von Frey filament (from North Coast Medical) in accordance with the method described in a known literature (Chaplan et al., Journal of Neuroscience Methods, vol. 53, p. 55-63, 1994).

The fibromyalgia syndrome model rats thus obtained are divided into groups such that the 50% response threshold (mean value of the right hind paw and the left hind paw) of the individual groups became equal, and a test compound was administered to the fibromyalgia syndrome model rats on seven days after the initial administration of acidic saline.

Figure 10:
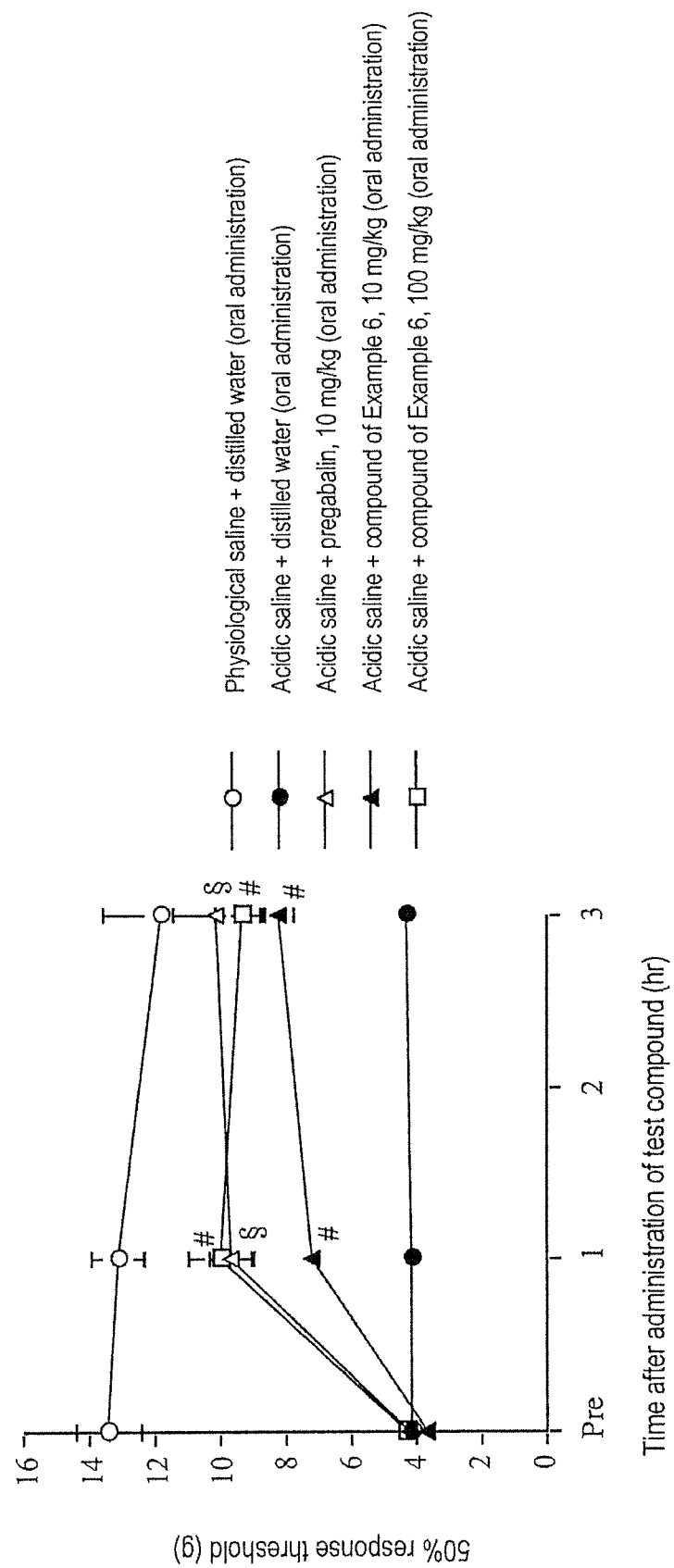
FIG. 10 is a graph showing the effect of the compound of Example 6 in a rat fibromyalgia model (oral administration).

The compounds of Examples 6 and 18 (10 to 100 mg/kg for the compound of Example 6; 1 to 100 mg/kg for the compound of Example 18) were separately dissolved in distilled water and orally administered to fibromyalgia model rats ("acidic saline+the compound of Example 6" in FIG. 10 and "acidic saline+the compound of Example 18" in FIG. 11). Pregabalin serving as a positive control (10 mg/kg; from KEMPROTEC) was dissolved in distilled water and then orally administered ("acidic saline+pregabalin" in FIG. 10 or 11). As a control, distilled water was orally administered to fibromyalgia syndrome model rats ("acidic saline+ distilled water" in FIG. 10 or 11). Furthermore, distilled water was orally administered to rats not afflicted with fibromyalgia syndrome ("physiological saline+distilled water" in FIG. 10 or 11). In one hour and three hours after the oral administration, allodynia in individual rats was measured to evaluate an analgesic action. At this time, the 50% response threshold value in the measurement of allodynia before oral administration of the test compound on seven days after initial administration of acidic saline was defined as the pre-value.

2. Results:

The results are shown in FIG. 10 or 11. In the figures, the vertical axis represents 50% response threshold (mean value of the right hind paw and the left hind paw) (g) (mean value±standard error, n=4 to 6). The higher numerical value indicates that allodynia is improved in the fibromyalgia syndrome model rats.

FIGS. 10 and 11 show the results of oral administration of the compounds of Examples 6 and 18, respectively. In the figures, the horizontal axis represents the time before oral administration of the compound of Example 6 or 18 (pre-value) and the passage of time (hr) from the oral administration of the compound of Example 6 or 18. In the figures, mark "§ or #" indicates that the value is statistically significant as a result of unpaired t-test, Welch's test, Williams test or Shirley-Williams test based on the "acidic saline+distilled water" group ("acidic saline+distilled water" in the figures) of every measurement time as a control (§: t-test or the Welch's test (p<0.05), #: the Williams test or Shirley-Williams test (p<0.025)).

In the group to which the compound of Example 6 or 18 was orally administered ("acidic saline+the compound of Example 6 or 18" in each figure), the allodynia observed in the fibromyalgia syndrome model rats was statistically significantly improved compared to the "acidic saline+distilled water" group, similarly to a positive control, i.e., the group to which pregabalin was orally administered ("acidic saline+ pregabalin" in each figure).

These results clearly demonstrated that a cyclic amine derivative (I) or a pharmacologically acceptable salt thereof is effective to fibromyalgia syndrome.

INDUSTRIAL APPLICABILITY

The cyclic amine derivative or a pharmacologically acceptable salt thereof can be used as medicines for pain symptoms since it can exhibit an analgesic action against pain, in particular, neuropathic pain or fibromyalgia syndrome.

The invention claimed is:

1. A cyclic amine derivative represented by general formula (I) or a pharmacologically acceptable salt thereof:

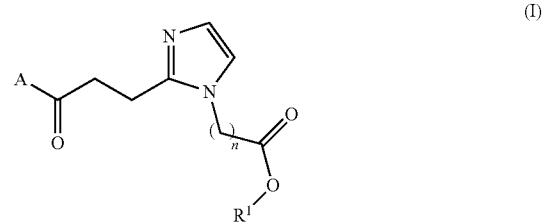

wherein A represents a group represented by formula (IIa) or (IIb),

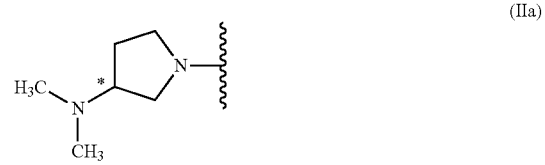

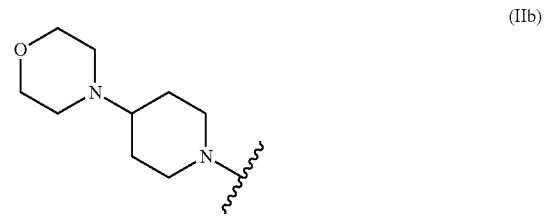

wherein the stereochemical configuration of the asymmetric carbon marked with * is S;
$R^1$ represents an alkyl group having 3 to 8 carbon atoms;
when A represents a group represented by the formula (IIa), n represents 2; and
when A represents a group represented by the formula (IIb), n represents 1.

2. The cyclic amine derivative or the pharmacologically acceptable salt thereof according to claim 1, wherein A is a group represented by formula (IIa).

3. The cyclic amine derivative or the pharmacologically acceptable salt thereof according to claim 2, wherein the cyclic amine derivative represented by formula (I) is a compound selected from the group consisting of
n-butyl (S)-3-(2-(3-(3-(dimethylamino)pyrrolidin-1-yl)-3-oxopropyl)-1H-imidazol-1-yl)propanoate,
n-hexyl (S)-3-(2-(3-(3-(dimethylamino)pyrrolidin-1-yl)-3-oxopropyl)-1H-imidazol-1-yl)propanoate,
n-heptyl (S)-3-(2-(3-(3-(dimethylamino)pyrrolidin-1-yl)-3-oxopropyl)-1H-imidazol-1-yl)propanoate, and n-octyl (S)-3-(2-(3-(3-(dimethylamino)pyrrolidin-1-yl)-3-oxopropyl)-1H-imidazol-1-yl)propanoate.

4. The cyclic amine derivative or the pharmacologically acceptable salt thereof according to claim 1, wherein A is a group represented by formula (IIb).

5. The cyclic amine derivative or the pharmacologically acceptable salt thereof according to claim 4, wherein the cyclic amine derivative represented by formula (I) is a compound selected from the group consisting of n-propyl 2-(2-(3-(4-morpholinopiperidin-1-yl)-3-oxopropyl)-1H-imidazol-1-yl)acetate, n-butyl 2-(2-(3-(4-morpholinopiperidin-1-yl)-3-oxopropyl)-1H-imidazol-1-yl)acetate, n-pentyl 2-(2-(3-(4-morpholinopiperidin-1-yl)-3-oxopropyl)-1H-imidazol-1-yl)acetate, n-hexyl 2-(2-(3-(4-morpholinopiperidin-1-yl)-3-oxopropyl)-1H-imidazol-1-yl)acetate, n-heptyl 2-(2-(3-(4-morpholinopiperidin-1-yl)-3-oxopropyl)-1H-imidazol-1-yl)acetate, and n-octyl 2-(2-(3-(4-morpholinopiperidin-1-yl)-3-oxopropyl)-1H-imidazol-1-yl)acetate.

6. A medicine comprising the cyclic amine derivative or the pharmacologically acceptable salt thereof according to claim 1 as an active ingredient.

7. An analgesic agent comprising the cyclic amine derivative or the pharmacologically acceptable salt thereof according to claim 1 as an active ingredient.

8. A therapeutic agent for neuropathic pain comprising the cyclic amine derivative or the pharmacologically acceptable salt thereof according to claim 1 as an active ingredient.

9. A therapeutic agent for fibromyalgia syndrome comprising the cyclic amine derivative or the pharmacologically acceptable salt thereof according to claim 1 as an active ingredient.

10. A method of treating pain comprising administering a therapeutically effective amount of the cyclic amine derivative or the pharmacologically acceptable salt thereof according to claim 1 to a patient in need thereof.

11. A method of treating neuropathic pain comprising administering a therapeutically effective amount of the cyclic amine derivative or the pharmacologically acceptable salt thereof according to claim 1 to a patient in need thereof.

12. A method of treating fibromyalgia syndrome comprising administering a therapeutically effective amount of the cyclic amine derivative or the pharmacologically acceptable salt thereof according to claim 1 to a patient in need thereof.

* * * * *